United States Patent
Echigo

(10) Patent No.: US 10,884,285 B2
(45) Date of Patent: Jan. 5, 2021

(54) IMAGING DEVICE

(71) Applicant: OLYMPUS CORPORATION, Hachioji (JP)

(72) Inventor: Hitoshi Echigo, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 330 days.

(21) Appl. No.: 15/933,965

(22) Filed: Mar. 23, 2018

(65) Prior Publication Data

US 2018/0210285 A1    Jul. 26, 2018

Related U.S. Application Data

(63) Continuation of application No. PCT/JP2015/078222, filed on Oct. 5, 2015.

(51) Int. Cl.
| | | |
|---|---|---|
| *G02F 1/1335* | (2006.01) | |
| *G03B 15/00* | (2006.01) | |
| (Continued) | | |

(52) U.S. Cl.
CPC ...... *G02F 1/133526* (2013.01); *G02F 1/1336* (2013.01); *G02F 1/13306* (2013.01); *G03B 5/00* (2013.01); *G03B 15/00* (2013.01); *G06K 9/209* (2013.01); *H04N 5/2254* (2013.01); *H04N 5/2256* (2013.01); *A61B 5/117* (2013.01); *G03B 19/023* (2013.01)

(58) Field of Classification Search
CPC ........... G02F 1/133526; G02F 1/13306; G02F 1/1336; G03B 15/00; G03B 5/00; G03B 19/023; H04N 5/2256; H04N 5/2254; G06K 9/209; A61B 5/117
See application file for complete search history.

(56) References Cited

U.S. PATENT DOCUMENTS

| | | | | |
|---|---|---|---|---|
| 2005/0001157 A1* | 1/2005 | Ishida | ................ | G02B 21/0044 250/234 |
| 2005/0122549 A1* | 6/2005 | Goulanian | ............... | G03H 1/30 359/3 |

(Continued)

FOREIGN PATENT DOCUMENTS

| | | |
|---|---|---|
| JP | 2010049664 A | 3/2010 |
| JP | 4748257 B2 | 8/2011 |

(Continued)

OTHER PUBLICATIONS

Office Action (Final Rejection) dated Apr. 12, 2019 issued in U.S. Appl. No. 15/425,884.

(Continued)

*Primary Examiner* — Nasim N Nirjhar
(74) *Attorney, Agent, or Firm* — Holtz, Holtz & Volek PC

(57) ABSTRACT

An imaging device includes an illuminator, a stage, a plurality of microlenses, an imaging element, and a controller. The controller is configured to control at least one of an irradiation position of light beams from the illuminator, and the position of the plurality of microlenses to realize a first state and a second state. A first angle of the light beams incident to each of the plurality of microlenses in the first state and a second angle of the light beams incident to each of the plurality of microlenses in the second state are different from each other.

11 Claims, 11 Drawing Sheets

(51) Int. Cl.
*G03B 5/00* (2006.01)
*H04N 5/225* (2006.01)
*G06K 9/20* (2006.01)
*G02F 1/133* (2006.01)
*G02F 1/13357* (2006.01)
*A61B 5/117* (2016.01)
*G03B 19/02* (2006.01)

(56) References Cited

U.S. PATENT DOCUMENTS

| | | |
|---|---|---|
| 2006/0291048 A1 | 12/2006 | Olszak et al. |
| 2010/0026453 A1 | 2/2010 | Yamamoto et al. |
| 2010/0046807 A1 | 2/2010 | Sato |
| 2010/0188739 A1 | 7/2010 | Watson |
| 2011/0013102 A1* | 1/2011 | Miyazaki .......... G02F 1/133526 349/5 |
| 2012/0200694 A1 | 8/2012 | Garsha et al. |
| 2013/0242079 A1 | 9/2013 | Zhou et al. |
| 2014/0118527 A1 | 5/2014 | Zhou et al. |
| 2014/0161369 A1 | 6/2014 | Ishihara |
| 2014/0313576 A1 | 10/2014 | Uhl et al. |
| 2015/0054979 A1 | 2/2015 | Ou et al. |
| 2015/0070511 A1 | 3/2015 | Williams |
| 2015/0278567 A1 | 10/2015 | Chen |
| 2016/0085078 A1 | 3/2016 | Ronen et al. |
| 2017/0146789 A1 | 5/2017 | Lansel |

FOREIGN PATENT DOCUMENTS

| | | |
|---|---|---|
| JP | 2013130981 A | 7/2013 |
| JP | 2014532197 A | 12/2014 |
| WO | 2013049646 A1 | 4/2013 |

OTHER PUBLICATIONS

International Search Report (ISR) and Written Opinion dated Jun. 7, 2016 issued in International Application No. PCT/US2015/052973.
International Search Report (ISR) dated Dec. 28, 2015 issued in International Application No. PCT/JP2015/078222.
Written Opinion dated Dec. 28, 2015 issued in International Application No. PCT/JP2015/078222.
Antony Orth, et al. "Microscopy with microlens arrays: high throughput, high resolution and light-field imaging," Optics Express, vol. 20, No. 12, Jun. 4, 2012, pp. 1-10.
U.S. Office Action dated Sep. 14, 2018 issued in U.S. Appl. No. 15/425,884.

* cited by examiner

IMAGING DEVICE

This application is a continuation application based on PCT International Patent Application No. PCT/JP2015/078222, filed Oct. 5, 2015, the content of which is incorporated herein by reference.

BACKGROUND OF THE INVENTION

Field of the Invention

The present invention relates to an imaging device.

Description of Related Art

An imaging device that uses a lens array in which a plurality of microlenses are arranged has been disclosed. For example, Japanese Patent Publication No. 4748257 discloses a biometric authentication device that includes a lens array and images a living body. In the microlenses which are used in the imaging device, a focal length is shorter and a working distance is shorter in comparison to an ordinary lens having the same numerical aperture (NA). Accordingly, there is an advantage in that reducing thickness of a device is possible.

Description will be given of image formation in an imaging device that uses the lens array. Light beams generated from a light source are absorbed and scattered by a sample. Light beams transmitted through the sample are transmitted through a stage. The light beams transmitted through the stage are condensed by microlenses. The light beams transmitted through the microlenses are incident to an imaging element, and images of the sample are funned on an imaging plane of the imaging element.

In a case where two axes perpendicular to an optical axis of the microlenses are defined as an X-axis and a Y-axis, image that is projected on the imaging element by each microlens is inverted in the X-direction and the Y-direction. Through processing of image signals output from the imaging element, the image projected by each microlens is inverted in the X-direction and the Y-direction, and respective images are joined to each other. According to this, a non-inverted sample image is obtained.

Each of a plurality of the microlenses forms an image. In a case where two images formed by two adjacent microlenses overlap each other, it is difficult to separate the two images, which overlap each other, by processing of the image signals.

It is preferable that a magnification of the microlenses is high to increase the amount of information that is obtained. In addition, it is preferable that a gap between two images, which are projected on the imaging element by two adjacent microlenses, is small to increase the amount of information that is obtained.

On the other hand, in a case where the magnification of the microlenses is greater than one, light beams from a partial region of the sample are not incident to the plurality of microlenses. Therefore, an image of the partial region of the sample is not projected on the imaging element. In consideration of this circumstance, the magnification of the microlenses is preferably one. In addition, it is preferable that plurality of microlenses are arranged so that a plurality of images projected on the imaging element by the plurality of microlenses do not overlap each other and a gap does not exist between the plurality of images projected on the imaging element by the plurality of microlenses. According to this, an image of the sample is acquired with efficiency.

When a distance between the microlenses and the sample or a distance between the microlenses and the imaging element varies, the size of the images that are formed by the microlenses varies. There is a possibility that overlapping of a plurality of images or a gap between the plurality of images may exist due to the variation in the size of the image.

FIG. 19 shows an example in which images formed by two adjacent microlenses overlap each other. In FIG. 19, cross-sections of an illuminator 1020, a sample 1090, microlenses 1040, and an imaging element 1050 are shown. The sample 1090 is irradiated with light beams generated from the illuminator 1020. For convenience, characters (A, B, C, D, E, F, G, and H) indicating regions of the sample 1090 are shown in the drawing. Light beams transmitted through the sample 1090 are incident to the microlenses 1040. FIG. 19 shows an aspect in which light beams are incident to two adjacent microlenses 1040.

Light beams transmitted through each of the two microlenses 1040 are projected on the imaging element 1050. Images which are projected on the imaging element 1050 by the two microlenses 1040 are schematically shown on a lower side of the imaging element 1050. An image IMG11 is formed by the left microlens 1040 to which light beams from the regions (A, B, C, D, and E) of the sample 1090 are incident. An image IMG12 is formed by the right microlens 1040 to which light beams from the regions (D, E, F, G, and H) of the sample 1090 are incident. In the imaging element 1050, the image IMG11 and the image IMG12 partially overlap each other. That is, a portion, which is formed by light beams from the regions (A and B) of the sample 1090, in the image IMG11, and a portion, which is formed by light beams from the regions (G and H) of the sample 1090, in the image IMG12 overlap each other. According to this, information of the regions disappears in image signals. In FIG. 19, positions of the image IMG11 and the image IMG12 have been vertically deviated from each other for convenience, but actually, the image IMG11 and the image IMG12 partially overlap each other.

SUMMARY OF THE INVENTION

According to a first aspect of the present invention, an imaging device includes an illuminator, a stage, a plurality of microlenses, an imaging element, and a controller. The illuminator is configured to generate light beams. A sample is disposed on the stage, and the light beams from the illuminator are transmitted through the stage. The plurality of microlenses are two-dimensionally arranged, and configured to condense the light beams which are transmitted through the sample and the stage. The light beams transmitted through the plurality of microlenses are incident to the imaging element, and the imaging element is configured to output image signals based on the light beams. The controller is configured to control at least one of an irradiation position of the light beams from the illuminator and a position of the plurality of microlenses to realize a first state and a second state. A first angle of the light beams incident to each of the plurality of microlenses in the first state and a second angle of the light beams incident to each of the plurality of microlenses in the second state are different from each other.

According to a second aspect of the present invention, in the imaging device according to the first aspect, the illuminator may be configured to generate parallel light beams.

According to a third aspect of the present invention, in the imaging device according to the first aspect, the controller may be configured to control the position of the plurality of microlenses in a direction parallel to a plane that passes through centers of two or more microlenses among the plurality of microlenses.

According to a fourth aspect of the present invention, in the imaging device according to the first aspect, the illuminator may include a light source and a diaphragm. The light source may be configured to generate the light beams. The diaphragm may be disposed between the light source and the sample, and may include an opening. The controller may be configured to control a position of the diaphragm so that a position of the opening in the first state and a position of the opening in the second state are different from each other.

According to a fifth aspect of the present invention, in the imaging device according to the first aspect, the illuminator may include a light source and a plurality of liquid crystal elements. The light source may be configured to generate the light beams. The plurality of liquid crystal elements may be two-dimensionally arranged between the light source and the sample, and may be configured to enter a transmission state in which the light beams are transmitted and a blocking state in which the light beams are blocked. The controller may be configured to control the plurality of liquid crystal elements so that the liquid crystal element among the plurality of liquid crystal elements disposed in a first region enters the transmission state in the first state and the liquid crystal element among the plurality of liquid crystal elements disposed in a second region different from the first region enters the blocking state in the first state. The controller may be configured to control the plurality of liquid crystal elements so that the liquid crystal element disposed in a third region different from the first region enters the transmission state in the second state and the liquid crystal element disposed in a fourth region different from the third region enters the blocking state in the second state.

According to a sixth aspect of the present invention, in the imaging device according to the first aspect, the controller may be configured to control both of the irradiation position of the light beams from the illuminator and the position of the plurality of microlenses.

According to a seventh aspect of the present invention, in the imaging device according to the first aspect, the controller may be configured to calculate at least one of the irradiation position of the light beams from the illuminator and the position of the plurality of the microlenses in the first state. The controller may be configured to calculate at least one of the irradiation position of the light beams from the illuminator and the position of the plurality of microlenses in the second state. The controller may be configured to control at least one of the irradiation position of the light beams from the illuminator and the position of the plurality of microlenses on the basis of the calculated positions.

According to an eighth aspect of the present invention, in the imaging device according to the first aspect, controller may be configured to determine an imaging region in the sample on the basis of the image signals. The controller may be configured to control at least one of the irradiation position of the light beams from the illuminator and the position of the plurality of microlenses so that a first imaging region and a second imaging region are different from each other. The first imaging region may be the imaging region in the sample through which the light beams incident to each of the plurality of microlenses are transmitted in the first state. The second imaging region may be the imaging region in the sample through which the light beams incident to each of the plurality of microlenses are transmitted in the second state.

DETAILED DESCRIPTION OF THE INVENTION

Figure 1:
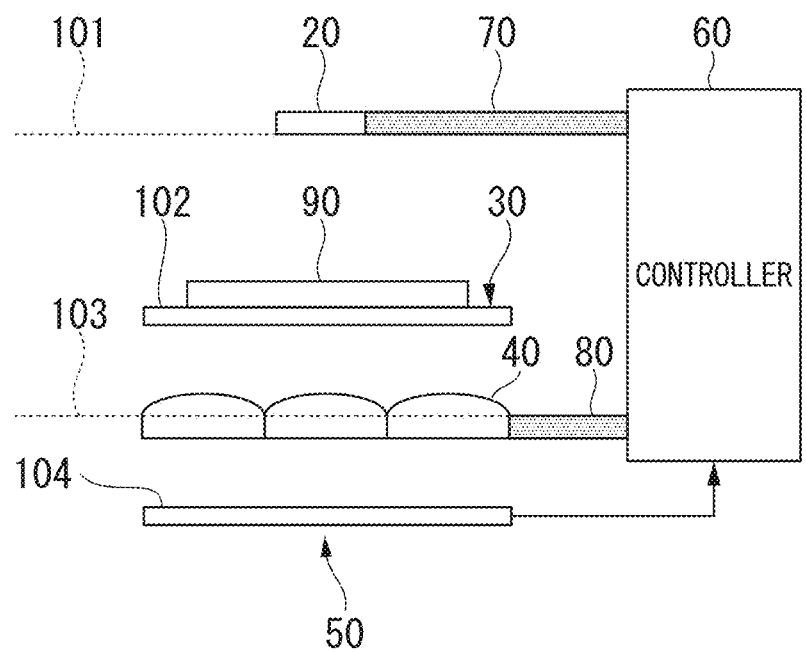
FIG. 1 is a block diagram showing a configuration of an imaging device according to an embodiment of the present invention.

An embodiment of the present invention will be described with reference to the drawings. FIG. 1 shows a configuration of an imaging device 10 according to the embodiment of the present invention. As shown in FIG. 1, the imaging device 10 includes an illuminator 20, a stage 30, a plurality of microlenses 40, an imaging element 50, and a controller 60. In addition, the imaging device 10 includes an illuminator drive unit 70 and a lens drive unit 80. In FIG. 1, cross-sections of the illuminator 20, the stage 30, the plurality of microlenses 40, and the imaging element 50 are shown. The cross-sections are perpendicular to a first plane 101 on which the illuminator 20 is disposed.

The illuminator 20 generates light beams. The illuminator 20 is disposed on the first plane 101 and generates light beams from the first plane 101. In FIG. 1, a cross-section of the first plane 101 is shown with a broken line.

For example, the illuminator 20 generates diffusing light beams. The illuminator 20 may generate parallel light beams. Examples of a light source that is used in the illuminator 20 include a laser diode (LD), a light-emitting diode (LED), and a halogen lamp. The light source that is used in the illuminator 20 may be a light source other than the above-described light sources. There is no limitation to a wavelength of the light beams generated by the light source that is used in the illuminator 20.

A sample 90 is disposed on the stage 30, and light beams from the illuminator 20 are transmitted through the stage 30. The stage 30 includes a second plane 102 on which the sample 90 is disposed. The light beams from the illuminator 20 are transmitted through the second plane 102. For example, the second plane 102 is parallel to the first plane 101.

For example, the stage 30 is formed of glass or acryl. The stage 30 has only to be formed from a material that can support the sample 90 and can allow light beams to be transmitted herethrough.

The plurality of microlenses 40 are two-dimensionally arranged and condense light beams which are transmitted through the sample 90 and the stage 30. In FIG. 1, a reference numeral of one microlens 40 is shown as a representative. For example, the centers (principal points) of two or more microlenses 40 are disposed on a third plane 103. That is, the third plane 103 is a plane that passes through the centers of two or more microlenses 40. The third plane 103 is parallel to the two-dimensional direction in which the plurality of microlenses 40 are arranged. For example, the third plane 103 is parallel to the first plane 101 or the second plane 102. In FIG. 1, a cross-section of the third plane 103 is shown with a broken line.

For example, the plurality of microlenses 40 are formed in an array shape with respect to one base body. The base body and the plurality of microlenses 40 are integrated with each other. The plurality of microlenses 40 may be individually formed. For example, the shape of the microlenses 40 is a circle. The shape of the microlenses 40 may be a polygon such as a triangle, a quadrangle, or a hexagon.

Generally, the microlenses 40 have aberration. Shading and distortion occur at the peripheral portion of an image, which is formed by the microlenses 40, due to an influence of aberration. At the central portion of the image formed by the microlenses 40, a favorable image, in which an influence of the shading and the distortion is reduced, is obtained.

Light beams transmitted through the plurality of microlenses 40 are incident to the imaging element 50. The imaging element 50 outputs image signals based on the light beams. The imaging element 50 includes a fourth plane 104 (imaging plane) on which a plurality of pixels, to which the light beams transmitted through the plurality of microlenses 40 are incident, are arranged. Each of the plurality of pixels outputs an image signal based on a light beam that is incident to each of the plurality of pixels.

For example, the imaging element 50 is an image sensor on which a complementary metal oxide semiconductor (CMOS) or a charge-coupled device (CCD) is mounted.

The stage 30 and the sample 90 are disposed between the illuminator 20 and the plurality of microlenses 40. The plurality of microlenses 40 are disposed between the stage 30 and the imaging element 50.

The controller 60 controls at least one of an irradiation position of light beams from the illuminator 20 and a position of the plurality of microlenses 40 so as to realize a first state and a second state. A first angle of light beams incident to each of the plurality of microlenses 40 in the first state, and a second angle of light beams incident to each of the plurality of microlenses 40 in the second state are different from each other.

The angle of light beams incident to each of the microlenses 40 is an angle at which a straight line passing through the center (center of gravity) of the illuminator 20 on the first plane 101 and the center (principal point) of the microlens 40 intersects the third plane 103. The center (center of gravity) of the illuminator 20 on the first plane 101 is the center (center of gravity) of a region in which light beams incident to the microlens 40 are generated. The center (center of gravity) of the illuminator 20 on the first plane 101 is not necessarily the center (center of gravity) of the entirety of the illuminator 20.

For example, the controller 60 controls an irradiation position of light beams from the illuminator 20. That is, the controller 60 moves the illuminator 20 in a direction parallel to the first plane 101. According to this, the controller 60 controls a position of the illuminator 20 in the direction parallel to the first plane 101. The controller 60 may move only partial elements included in the illuminator 20 in the direction parallel to the first plane 101. According to this, the controller 60 may control a position of the partial elements included in the illuminator 20 in the direction parallel to the first plane 101. The controller 60 may move a light-emitting region of the illuminator 20 in the direction parallel to the first plane 101 by changing a state of the partial elements included in the illuminator 20. According to this, the controller 60 may control a position of the light-emitting region of the illuminator 20 in the direction parallel to the first plane 101.

Alternatively, the controller 60 controls the position of the plurality of microlenses 40. That is, the controller 60 moves the plurality of microlenses 40 in a direction parallel to the third plane 103. According to this, the controller 60 controls the position of the plurality of microlenses 40 in the direction parallel to the third plane 103.

Alternatively, the controller 60 controls both of the irradiation position of light beams from the illuminator 20, and the position of the plurality of microlenses 40. That is, the controller 60 moves the illuminator 20 in a direction parallel to the first plane 101, and moves the plurality of microlenses 40 in a direction parallel to the third plane 103. According to this, the controller 60 controls the position of the illuminator 20 in the direction parallel to the first plane 101, and the position of the plurality of microlenses 40 in the direction parallel to the third plane 103. The control of the position of the illuminator 20 may be control of a position of partial elements included in the illuminator 20. The control of the position of the illuminator 20 may be a control of a position of a emitting light region of the illuminator 20 through a state control of partial elements included in the illuminator 20.

The controller 60 combine first image signals generated in the first state and second image signals generated in the second state to generate image signals of the sample 90. At this time, the controller 60 cuts out a region, which corresponds to an image formed by each of the plurality of microlenses 40, in a first image based on the first image signals. That is, the controller 60 generates a first image signal, which corresponds to an image formed by each of the plurality of microlenses 40, from the first image signals corresponding to the entirety of the imaging plane of the imaging element 50. Similarly, the controller 60 cuts out a region, which corresponds to an image formed by each of the plurality of microlenses 40, in a second image based on the second image signals. That is, the controller 60 generates a second image signal, which corresponds to an image formed by each of the plurality of microlenses 40, from the second image signals corresponding to the entirety of the imaging plane of the imaging element 50. The controller 60 can reduce an influence of a gap, which exists between two images projected on the imaging element 50 by two adjacent microlenses 40, through the above-described processing.

When the region corresponding to the image formed by each of the plurality of microlenses 40 is cut out, the controller 60 may cut out a region that corresponds to a part of the image formed by each of the microlenses 40. That is, the controller 60 may cut out a region corresponding to an image necessary for combination from an image formed by each of the microlenses 40. For example, in an image formed by each of the microlenses 40, the controller 60 cuts out a region other than a region that overlaps an image formed by another microlens 40. Alternatively, the controller 60 cuts out only the central image region in an image formed by each of the microlenses 40. The controller 60 combines a first image signal and a second image signal which correspond to the cut-out regions.

For example, the controller 60 includes a processor such as a central processing unit (CPU), a digital signal processor (DSP), a graphics processing unit (GPU), or the like. The controller 60 may include hardware such as an application specific integrated circuit (ASIC), a field-programmable gate array (FPGA), or the like. The controller 60 may include an image processing circuit that processes an image signal. Alternatively, the imaging device 10 may include an image processing circuit that is independent from the controller 60.

The illuminator drive unit 70 moves the illuminator 20 in a direction parallel to the first plane 101. The lens drive unit 80 moves the plurality of microlenses 40 in a direction parallel to the third plane 103. The illuminator drive unit 70 and the lens drive unit 80 are controlled by the controller 60. The controller 60 controls an irradiation position of light beams from the illuminator 20 through the illuminator drive unit 70. The controller 60 controls the position of the plurality of microlenses 40 through the lens drive unit 80.

The imaging device 10 may include only one of the illuminator drive unit 70 and the lens drive unit 80.

The illuminator drive unit 70 and the lens drive unit 80 convert a force of a motor in a rotary direction into a force in a linear direction by a ball screw and the like. Examples of the motor that is used in the illuminator drive unit 70 and the lens drive unit 80 include a stepping motor and a brushless motor. The motor that is used in the illuminator drive unit 70 and the lens drive unit 80 may be a motor other than the above-described motors.

Figure 2:
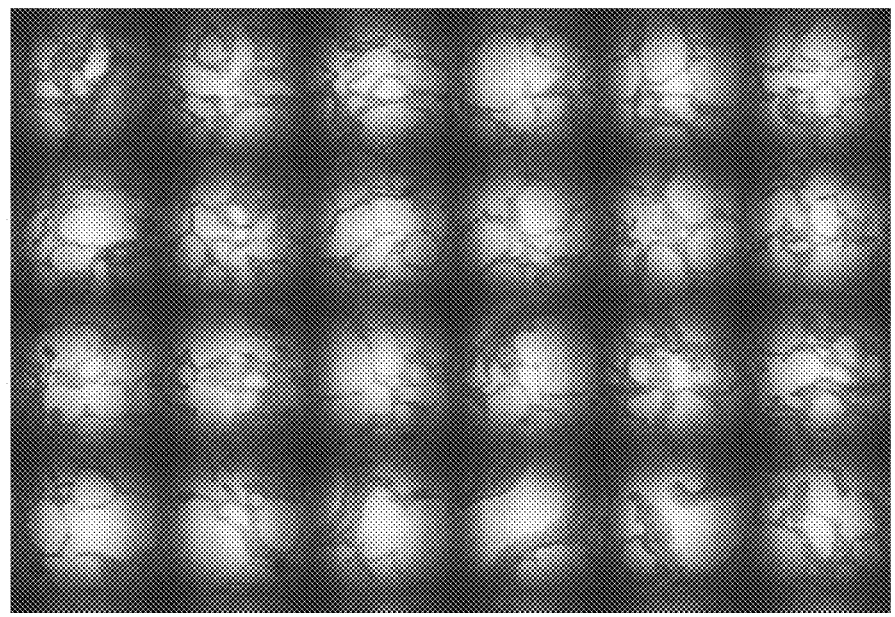
FIG. 2 is a reference view showing images that are projected on an imaging element by a plurality of microlenses according to the embodiment of the present invention.

FIG. 2 shows images that are projected on the imaging element 50 by the plurality of microlenses 40. Since the plurality of microlenses 40 are two-dimensionally arranged, a plurality of images projected by the plurality of microlenses 40 are two-dimensionally arranged. In FIG. 2, a gap exists between two images which are projected on the imaging element 50 by two adjacent microlenses 40 among the plurality of microlenses 40.

In a case where the size of the images formed by the plurality of microlenses 40 is smaller than the pitch of the images, a gap which light beams do not reach exists between the images on the imaging plane of the imaging element 50. An image signal, which is output from a pixel disposed in the gap, does not include image information. The controller 60 can reduce the influence of the gap by generating an image signal, which corresponds to an image formed by each of the plurality of microlenses 40, from image signals corresponding to the entirety of the imaging plane of the imaging element 50.

In a case where the size of the images formed by the plurality of microlenses 40 is greater than the pitch of the images, a plurality of images overlap each other on the imaging plane of the imaging element 50. A plurality of pieces of information of the images are mixed in image signals output from a pixel that is disposed at a portion at which the plurality of images overlap each other. The controller 60 cannot separate the plurality of pieces of information which are mixed. That is, the controller 60 cannot acquire information of the sample 90 from image signals at a portion in which a plurality of images overlap each other.

Figure 3:
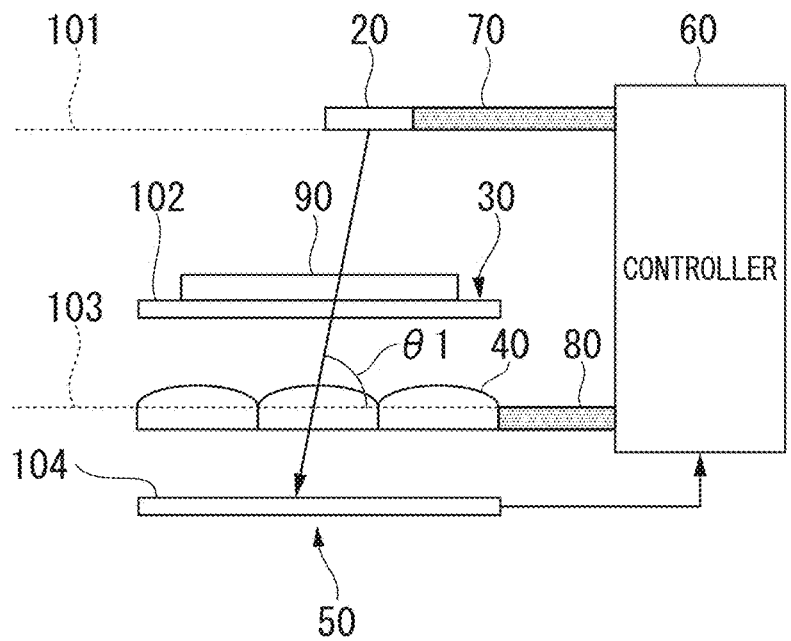
FIG. 3 is a block diagram showing a state of the imaging device in a first state and a second state according to the embodiment of the present invention.
Figure 4:
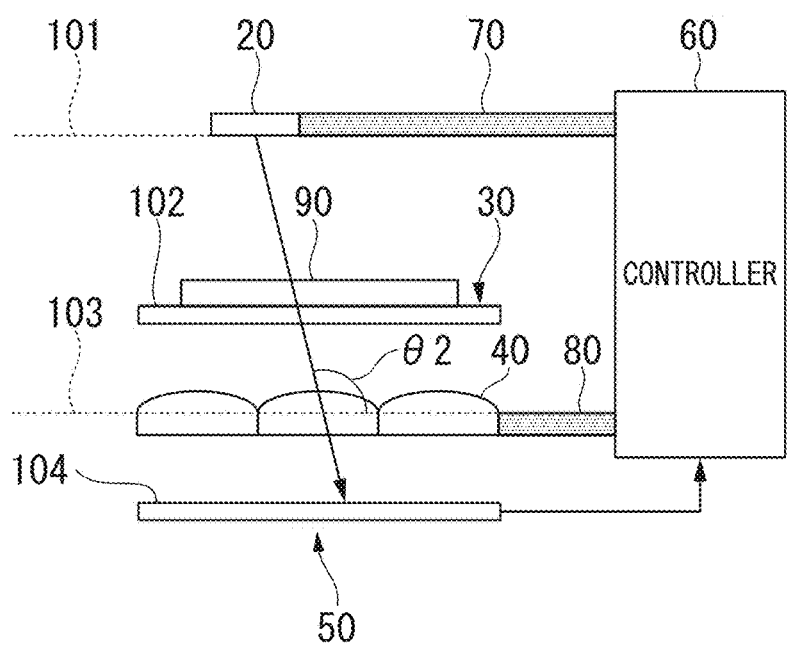
FIG. 4 is a block diagram showing a state of the imaging device in the first state and the second state according to the embodiment of the present invention.

FIG. 3 and FIG. 4 show the state of the imaging device 10 in the first state and the second state. FIG. 3 shows an example of the first state, and FIG. 4 shows an example of the second state. Cross-sections of the illuminator 20, the stage 30, the plurality of microlenses 40, and the imaging element 50 are shown in FIG. 3 and FIG. 4. The cross-sections are perpendicular to the first plane 101 on which the illuminator 20 is disposed. FIG. 3 and FIG. 4 show an example in which the illuminator 20 is moved in a direction parallel to the first plane 101.

As shown in FIG. 3, in the first state, a first angle of light beams incident to a central microlens 40 among the plurality of microlenses is θ1. FIG. 4 shows a state after the illuminator 20 is moved to the left side. The angle of light beams incident to the central microlens 40 varies due to the movement of the illuminator 20. As shown in FIG. 4, in the second state, a second angle of light beams incident to the central microlens 40 is θ2. The first angle θ1 and the second angle θ2 are different from each other. An angle of light beams incident to each of the microlenses 40 is an angle at which a straight line passing through the center (center of gravity) of the illuminator 20 on the first plane 101 and the center (principal point) of the microlens 40 intersects the third plane 103.

FIG. 3 and FIG. 4 show a variation of an angle of light beams incident to the central microlens 40. Similarly, an angle of light beams incident to the other microlenses 40 also varies. When the angle of light beams incident to the plurality of microlenses 40 varies, regions of the sample 90 in images that are projected on the imaging element 50 by the plurality of microlenses 40 vary.

Figure 5:
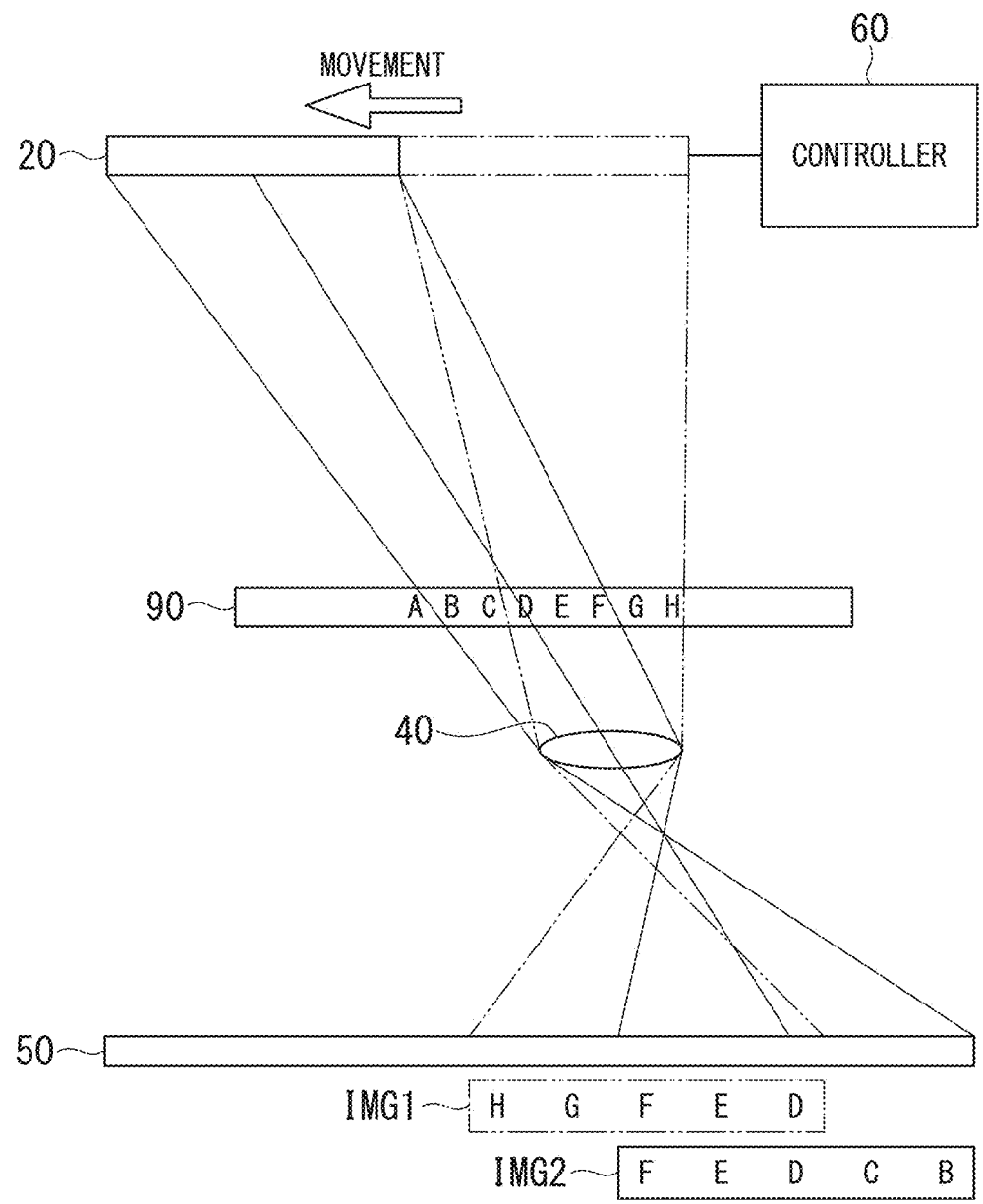
FIG. 5 is a schematic view showing a variation of the images that are projected on the imaging, element by the plurality of microlenses according to the embodiment of the present invention.

FIG. 5 shows a variation of images that are projected on the imaging element 50 by the plurality of microlenses 40. Cross-sections of the illuminator 20, the sample 90, one of the microlenses 40, and the imaging element 50 are shown in FIG. 5. The sample 90 is irradiated with light beams generated from the illuminator 20. For convenience, letters (A, B, C, D, E, F, G, and H) indicating regions of the sample 90 are shown in the drawing. Light beams transmitted through the sample 90 are incident to the microlenses 40. FIG. 5 shows an aspect in which light beams are incident to one microlens 40 among the plurality of microlenses 40.

Light beams transmitted through the microlens 40 are projected on the imaging element 50. Images, which are projected on the imaging element 50 by the plurality of microlenses 40, are schematically shown on a lower side of the imaging element 50. The illuminator 20 in the first state and a luminous flux at that time are indicated by a broken line. The illuminator 20 in the second state and a luminous flux at that time are indicated by a solid line.

In the first state, when light beams from regions (D, E, F, G, and H) of the sample 90 are incident to the microlens 40, an image IMG1 is formed. When light beams from regions (B, C, D, E, and F) of the sample 90 are incident to the microlens 40, an image IMG2 is formed. In the image IMG1, an image of the region (D) of the sample 90 exists at the peripheral portion of the image IMG1. On the other hand, in the image IMG2, an image of the region (D) of the sample 90 exists at the central portion of the image IMG2. Images of the regions (G and H) of the sample 90 are included in the image IMG1 but are not included in the image IMG2. Images of the regions (B and C) of the sample 90 are included in the image IMG2 but are not included in the image IMG1. That is, when an angle of light beams incident to the microlens 40 varies, regions of the sample 90 in images that are projected on the imaging element 50 by the plurality of microlenses 40 vary. When the controller 60 controls an irradiation position of light beams from the illuminator 20, the peripheral portion of the image formed by the microlens 40 in the first state and the central portion of the image formed by the microlens 40 in the second state match each other.

In the image IMG1, an image of the region (D) of the sample 90 is influenced by aberration. On the other hand, in the image IMG2, the influence of aberration on the image of the region (D) of the sample 90 is reduced.

For example, the controller 60 cuts out an image of the regions (E, F, and G) of the sample 90 on a central side of the image IMG1 from images corresponding to the image IMG1. Similarly, the controller 60 cuts out an image of the regions (C, D, and E) of the sample 90 on a central side of the image IMG2 from images corresponding to the image IMG2. The controller 60 combines the two images which are cut out in such a manner that images of the region (E) of the sample 90 overlap each other, thereby obtaining an image of the regions (C, D, E, F, and G) of the sample 90. The controller 60 combines images projected on the imaging element 50 by each of the plurality of microlenses 40, thereby obtaining an image of the regions (A, B, C, D, E, F, G, and H) of the sample 90.

As described above, when the illuminator 20 moves, an angle of light beams incident to the plurality of microlenses 40 varies, and regions of the sample 90 in images that are projected on the imaging element 50 by the plurality of microlenses 40 vary.

Figure 6:
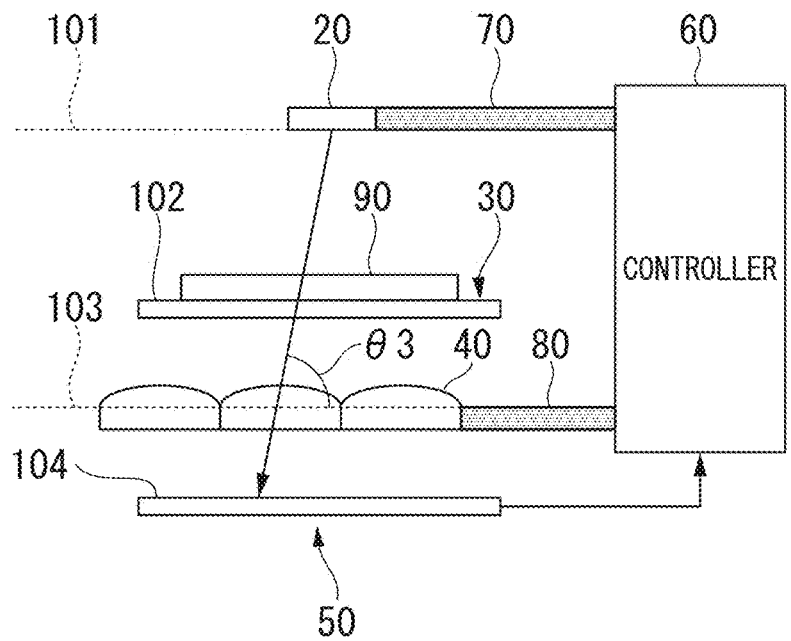
FIG. 6 is a block diagram showing a state of the imaging device in the first state and the second state according to the embodiment of the present invention.
Figure 7:
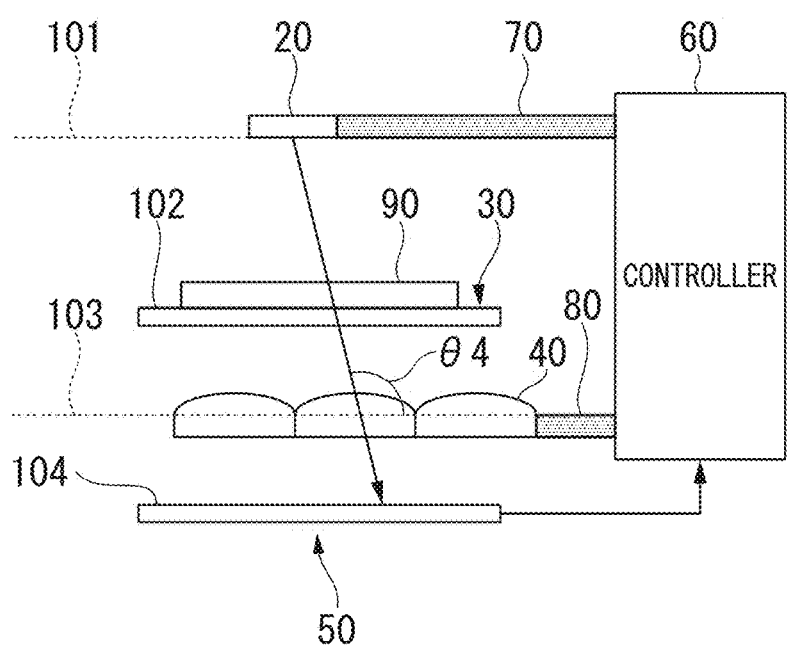
FIG. 7 is a block diagram showing a state of the imaging device in the first state and the second state according to the embodiment of the present invention.

The plurality of microlenses 40 may be moved in a direction parallel to the third plane 103. FIG. 6 and FIG. 7 show a state of the imaging device 10 in the first state and the second state. FIG. 6 shows an example in the first state, and FIG. 7 shows an example in the second state. Cross-sections of the illuminator 20, the stage 30, the plurality of microlenses 40, and the imaging element 50 are shown in FIG. 6 and FIG. 7. The cross-sections are perpendicular to the first plane 101 on which the illuminator 20 is disposed. FIG. 6 and FIG. 7 show an example in which the plurality of microlenses 40 are moved in a direction parallel to the third plane 103.

As shown in FIG. 6, in the first state, a first angle of light beams incident to the central microlens 40 is θ3. FIG. 7 shows a state after the plurality of microlenses 40 are moved to the right side. When the plurality of microlenses 40 are moved, an angle of light beams incident to the central microlens 40 varies. As shown in FIG. 7, in the second state, a second angle of light beams incident to the central microlens 40 is θ4. The first angle θ3 and the second angle θ4 are different from each other. The angle of light beams incident to each of the microlenses 40 is an angle at which a straight line passing through the center (center of gravity) of the illuminator 20 on the first plane 101 and the center (principal point) of the microlens 40 intersects the third plane 103.

FIG. 6 and FIG. 7 show a variation of an angle of light beams incident to the central microlens 40. Similarly, an angle of light beams incident to the other microlenses 40 also varies. When the angle of light beams incident to the plurality of microlenses 40 varies, regions of the sample 90 in images that are projected on the imaging element 50 by the plurality of microlenses 40 vary.

Figure 8:
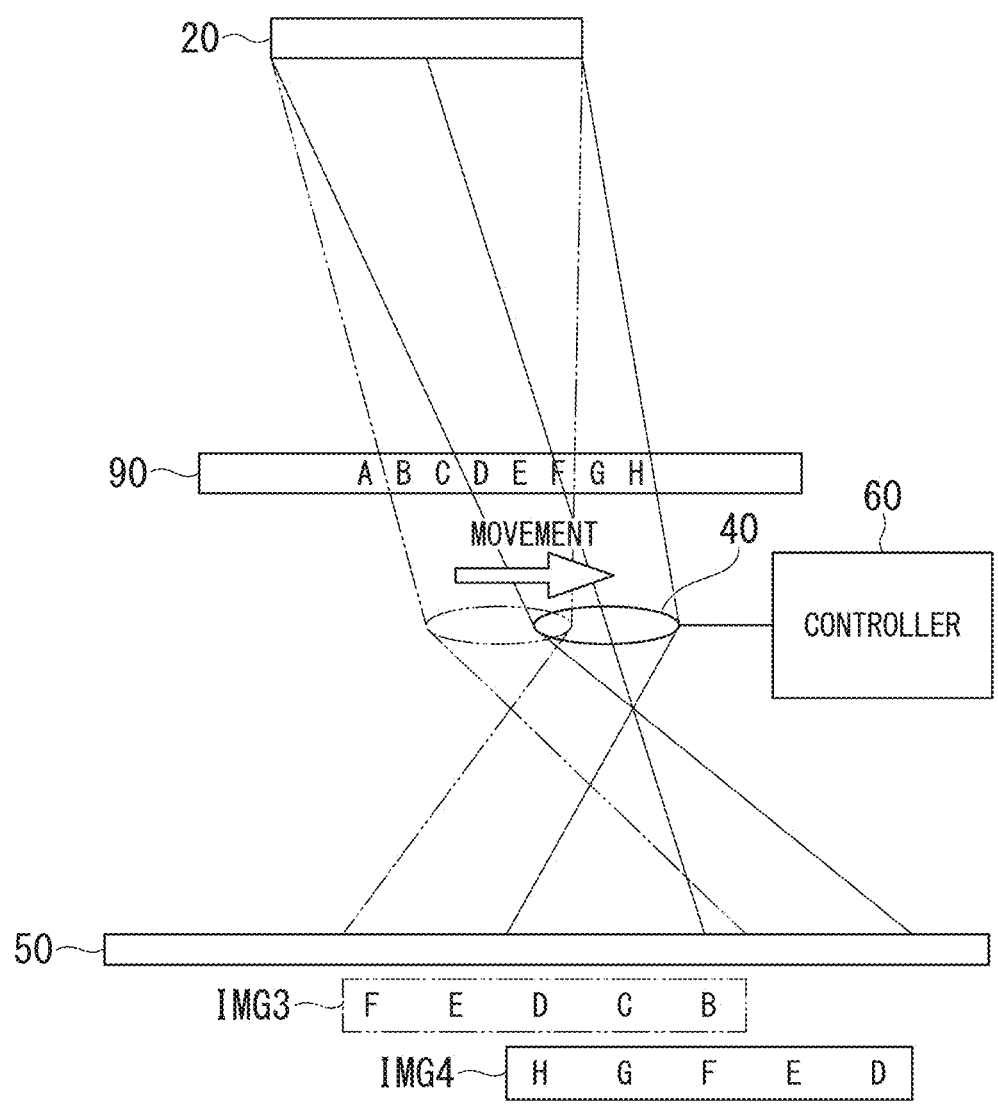
FIG. 8 is a schematic view showing a variation of the images that are projected on the imaging element by the plurality of microlenses according to the embodiment of the present invention.

FIG. 8 shows a variation of images that are projected on the imaging element 50 by the plurality of microlenses 40. Cross-sections of the illuminator 20, the sample 90, one of the microlenses 40, and the imaging element 50 are shown in FIG. 8. The sample 90 is irradiated with light beams generated from the illuminator 20. For convenience, letters (A, B, C, D, E, F, G, and H) indicating regions of the sample 90 are shown in the drawing. Light beams transmitted through the sample 90 are incident to the microlenses 40. FIG. 8 shows an aspect in which light beams are incident to one microlens 40 among the plurality of microlenses 40.

Light beams transmitted through the microlens 40 are projected on the imaging element 50. Images, which are projected on the imaging element 50 by the plurality of microlenses 40, are schematically shown on a lower side of the imaging element 50. The microlens 40 in the first state and a luminous flux at that time are indicated by a broken line. The microlens 40 in the second state and a luminous flux at that time are indicated by a solid line.

In the first state, when light beams from regions (B, C, D, E, and F) of the sample 90 are incident to the microlens 40, an image IMG3 is formed. When light beams from regions (D, E, F, G, and H) of the sample 90 are incident to the microlens 40, an image IMG4 is formed. In the image IMG3, an image of the region (F) of the sample 90 exists at the peripheral portion of the image IMG3. On the other hand, in the image IMG4, an image of the region (F) of the sample 90 exists at the central portion of the image IMG4. Images of the regions (B and C) of the sample 90 are included in the image IMG3 but are not included in the image IMG4. Images of the regions (G and H) of the sample 90 are included in the image IMG4 but are not included in the image IMG3. That is, when an angle of light beams incident to the microlens 40 varies, regions of the sample 90 in images that are projected on the imaging element 50 by the plurality of microlenses 40 vary. When the controller 60 controls the position of the plurality of microlenses 40, the peripheral portion of the image formed by the microlens 40 in the first state and the central portion of the image formed by the microlens 40 in the second state match each other.

In the image IMG3, an image of the region (F) of the sample 90 is influenced by aberration. On the other hand, in the image IMG4, the influence of aberration on the image of the region (F) of the sample 90 is reduced.

For example, the controller 60 cuts out an image of the regions C, D, and E of the sample 90 on a central side of the image IMG3 from images corresponding to the image IMG3. Similarly, the controller 60 cuts out an image of the regions (E, F, and G) of the sample 90 on a central side of the image IMG4 from images corresponding to the image IMG4. The controller 60 combines the two images which are cut out in such a manner that images of the region (E) of the sample 90 overlap each other, thereby obtaining an image of the regions (C, D, E, F, and G) of the sample 90. The controller 60 combines images projected on the imaging element 50 by each of the plurality of microlenses 40, thereby obtaining an image of the regions (A, B, C, D, E, F, G, and H) of the sample 90.

As described above, when the plurality of microlenses 40 move, an angle of light beams incident to the plurality of microlenses 40 varies, and regions of the sample 90 in images that are projected on the imaging element 50 by the plurality of microlenses 40 vary.

It is not necessary for the illuminator 20 to be moved. Since the illuminator 20 provided with electrical wiring is fixed, a failure risk is reduced.

The illuminator 20 may generate parallel light beams. In this case, the size of images which are projected on the imaging element 50 by the plurality of microlenses 40 is constant regardless of a variation of a distance between the illuminator 20 and the plurality of microlenses 40. According to this, adjustment of the distance between the illuminator 20 and the plurality of microlenses 40 is simplified. In a case where the illuminator 20 generate parallel light beams, the first state and the second state are realized through movement of the plurality of microlenses 40.

The controller 60 may move both of the illuminator 20 and the plurality of microlenses 40. In this case, movement time and a movement distance of the illuminator 20 and the plurality of microlenses 40 are reduced.

Figure 9:
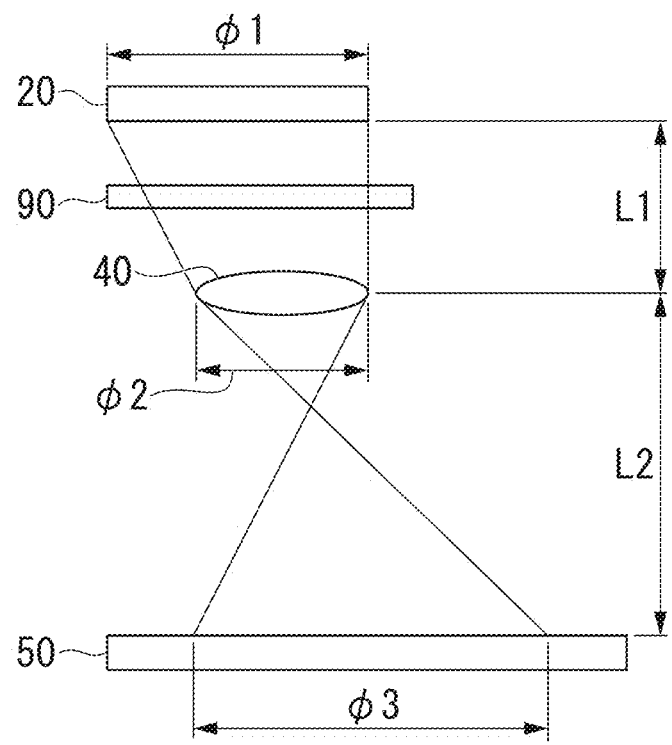
FIG. 9 is a schematic view showing a method of determining an irradiation position of light beams from an illuminator, or a position of the plurality of microlenses according to the embodiment of the present invention.
Figure 10:
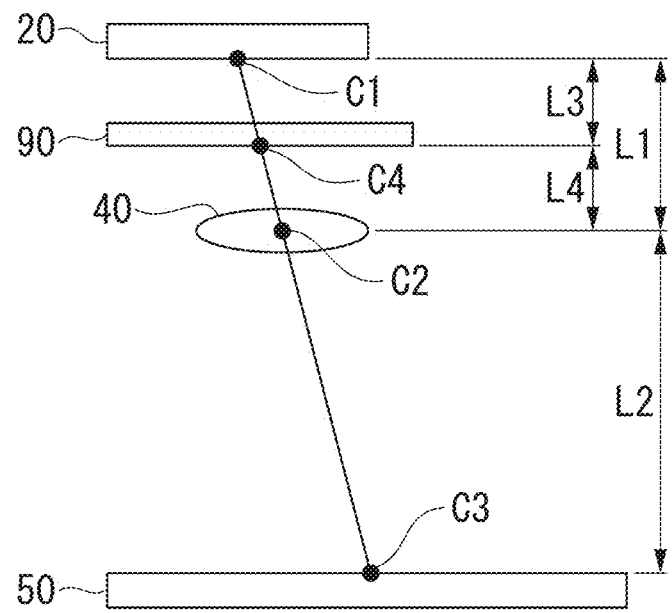
FIG. 10 is a schematic view showing the method of determining the irradiation position of light beams from the illuminator, or the position of the plurality of microlenses according to the embodiment of the present invention.
Figure 11:
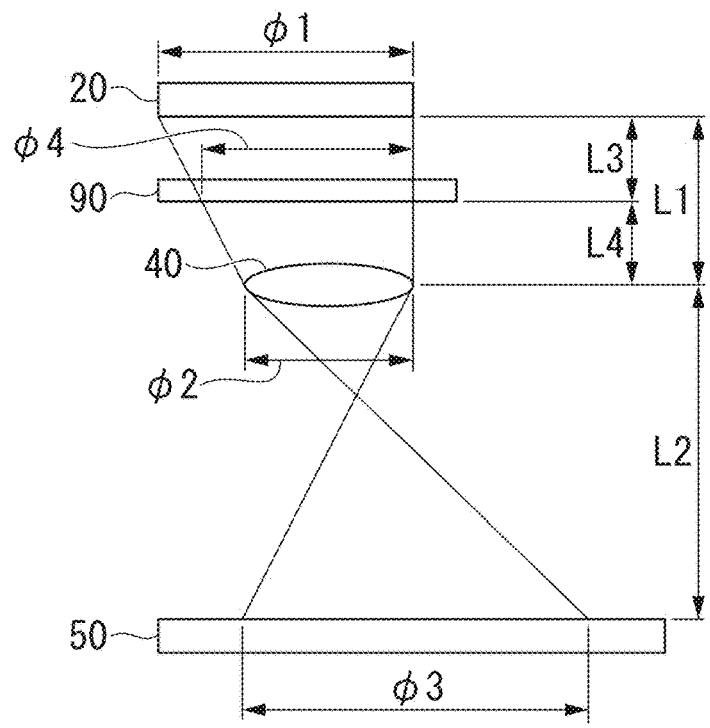
FIG. 11 is a schematic view showing the method of determining the irradiation position of light beams from the illuminator, or the position of the plurality of microlenses according to the embodiment of the present invention.

Description will be given of a method of determining the irradiation position of light beams from the illuminator 20 and the position of the plurality of microlenses 40 with reference to FIG. 9, FIG. 10, and FIG. 11. In FIG. 9, FIG. 10, and FIG. 11, cross-sections of the illuminator 20, the sample 90, one of the microlenses 40, and the imaging element 50 are shown. The cross-sections pass through the center of the microlens 40.

In a case where the sample 90 is thick, it is necessary to observe the sample 90 while moving a focal point in an optical axial direction of the microlens 40. The imaging device 10 can move the focal point in the optical axial direction of the microlens 40 by changing the distance between the sample 90 and the microlens 40.

In a case where illumination light beams are light beams other than parallel light beams, the size $\phi 3$ of an image that is projected on the imaging element 50 by the microlens 40 is calculated by Expression (1). In Expression (1), $\phi 1$ is a diameter illuminator 20. $\phi 2$ is a diameter of the microlens 40. L1 is a distance between the illuminator 20 and the microlens 40. L2 is a distance between the microlens 40 and the imaging element 50. f is a focal length of the microlens 40.

[Math. 1]

$$\phi_3 = \phi_2\left(\frac{L_2 - f}{f}\right) - \frac{L_2}{L_1}(\phi_2 - \phi_2) \qquad (1)$$

FIG. 9 shows a relationship between the diameter $\phi 1$ of the illuminator 20, the diameter $\phi 2$ of the microlens 40, and the size $\phi 3$ of the image. In addition, FIG. 9 shows a relationship between the distance L1 between the illuminator 20 and the microlens 40, and the distance L2 between the microlens 40 and the imaging element 50.

Expression (1) shows the size $\phi 3$ of the image in one dimension. The controller 60 calculates the size of the image in two dimensions by applying Expression (1) to two dimensions. In a case where the illuminator 20 generates parallel light beams, the diameter $\phi 1$ of the illuminator 20 in Expression (1) is the same as the diameter $\phi 2$ of the microlens 40.

In a case where the illumination light beams are light beams other than parallel light beams, a position C3 of the center (center of gravity) of an image that is projected on the imaging element 50 by the microlens 40 is calculated by Expression (2). In Expression (2), C1 is a position of the center (center of gravity) of the illuminator 20. C2 is a position of the center (principal point) of the microlens 40. L1 is a distance between the illuminator 20 and the microlens 40. L2 is a distance between the microlens 40 and the imaging element 50.

[Math. 2]

$$C_3 = C_2 - \frac{L_2}{L_1}(C_1 - C_2) \qquad (2)$$

In a case where the illumination light beams are light beams other than parallel light beams, a position C4 of the center (center of gravity) of the sample 90, which corresponds to the central position C3 of the image projected on the imaging element 50 by the microlens 40, is calculated by Expression (3). In Expression (3), C1 is a position of the center (center of gravity) of the illuminator 20. C2 is a position of the center (principal point) of the microlens 40. L3 is a distance between the illuminator 20 and the sample 90. L4 is a distance between the sample 90 and the microlens 40.

[Math. 3]

$$C_4 = C_1 - \frac{L_3}{L_3 + L_4}(C_1 - C_2) \qquad (3)$$

FIG. 10 shows a relationship between the central position C1 of the illuminator 20, the central position C2 of the microlens 40, the central position C3 of the image, and the central position C4 of the sample 90. In addition, FIG. 10 shows a relationship between the distance L1 between the illuminator 20 and the microlens 40, the distance L2 between the microlens 40 and the imaging element 50, the distance L3 between the illuminator 20 and the sample 90, and the distance L4 between the sample 90 and the microlens 40. The central position C3 of the image and the central position C4 of the sample 90 are on a straight line that passes through the central position C1 of the illuminator 20 and the central position C2 of the microlens 40.

Expression (2) shows the central position C3 of the image in one dimension. The controller 60 calculates the central position of the image in two dimensions by applying Expression (2) to two dimensions. In a case where the illuminator 20 generates parallel light beams, the central position C1 of the illuminator 20 in Expression (2) is the same as the central position C2 of the microlens 40.

Expression (3) shows the central position C4 of the sample 90 in one dimension. The controller 60 calculates the central position of the sample 90 in two dimensions by applying Expression (3) to two dimensions. In a case where the illuminator 20 generates parallel light beams, the central position C1 of the illuminator 20 in Expression (3) is the same as the central position C2 of the microlens 40.

In a case where the illumination light beams are light beams other than parallel light beams, the size φ4 of the sample 90, which corresponds to the size φ3 of the image projected on imaging element 50 by the microlens 40, is calculated by Expression (4). In Expression (4), φ1 is the diameter of the illuminator 20. φ2 is the diameter of the microlens 40. L3 is the distance between the illuminator 20 and the sample 90. L4 is the distance between the sample 90 and the microlens 40.

[Math. 4]

$$\phi_4 = \frac{L_4}{L_3 + L_4}(\phi_1 - \phi_2) + \phi_2 \quad (4)$$

FIG. 11 shows a relationship between the diameter φ1 of the illuminator 20, the diameter φ2 of the microlens 40, the size φ3 of the image, and the size φ4 of the sample 90. In addition, FIG. 11 shows a relationship between the distance L1 between the illuminator 20 and the microlens 40, the distance L2 between the microlens 40 and the imaging element 50, the distance L3 between the illuminator 20 and the sample 90, and the distance L4 between the sample 90 and the microlens 40. The size φ4 of the sample 90 is the size of regions of the sample 90 through which a luminous flux for projecting an image having the size φ3 on the imaging element 50 is transmitted.

Expression (4) shows the size φ4 of the sample 90 in one dimension. The controller 60 calculates the size of the sample 90 in two dimensions by applying Expression (4) to two dimensions. In a case where the illuminator 20 generates parallel light beams, the diameter φ1 of the illuminator 20 in Expression (4) is the same as the diameter φ2 of the microlens 40.

The sizes and the central positions, which are calculated by Expressions (1) to (4), are not influenced by the sample 90.

The controller 60 can calculate a region of the imaging element 50, on which an image is projected, by calculating the central position C3 of an image and the size θ3 of the image. The controller 60 can calculate regions of the sample 90, which correspond to the image projected on the imaging element 50, by calculating the central position C4 of the sample 90 and the size φ4 of the sample 90. That is, the controller 60 can determine a positional relationship between regions of the sample 90 and regions of the imaging element 50 on which the image is projected. The controller 60 determines regions of the sample 90, which correspond to image signals output from pixels in predetermined regions of the imaging element 50, on the basis of the positional relationship.

The controller 60 performs calculation by using Expressions (1) to (4) with respect to each of the plurality of microlenses 40. The controller 60 determines whether or not two images projected by two adjacent microlenses 40 overlap each other in the imaging element 50 on the basis of the calculation results. In a case where the two images overlap each other, the controller 60 determines regions of the sample 90 which correspond to a portion in which the two images overlap each other. The controller 60 cannot acquire information of the sample 90 front image signals of the portion in which the two images overlap each other, and can acquire information of the sample 90 from image signals from portions in which the two images do not overlap each other. The controller 60 repeats the above-described processing with respect to each of the two adjacent microlenses 40 to determine the regions of the sample 90 of which information can be acquired and the regions of the sample 90 of which information cannot be acquired.

At least one of the central position C1 and the central position C2 is changed, and then the above-described processing is performed. The central position C1 corresponds to an irradiation position of light beams from the illuminator 20. The central position C2 corresponds to the position of the plurality of microlenses 40. The controller 60 calculates at least one of the irradiation position of light beams from the illuminator 20, and the position of the plurality of microlenses 40 in the first state. The controller 60 calculates at least one of the irradiation position of light beams from the illuminator 20, and the position of the plurality of microlenses 40 in the second state. The controller 60 controls at least one of the irradiation position of light beams from the illuminator 20, and the position of the plurality of microlenses 40 on the basis of the position that is calculated. That is, the controller 60 moves the illuminator 20 so that the irradiation position of light beams from the illuminator 20 becomes the position that is calculated with respect to each of the first state and the second state. Alternatively, the controller 60 moves the plurality of microlenses 40 so that the position of the plurality of microlenses 40 becomes the position that is calculated with respect to each of the first state and the second state.

The controller 60 calculates at least one of the irradiation position of light beams from the illuminator 20 and the position of the plurality of microlenses 40 in a plurality of states including the first state and the second state. The controller 60 controls at least one of the irradiation position of light beams from the illuminator 20 and the position of the plurality of microlenses 40 on the basis of the position that is calculated with respect to each of the states.

In the plurality of states including the first state and the second state, at least one of the distance L1, the distance L2, the distance L3, and the distance L4 may be changed.

Image signals are acquired in the plurality of states including the first state and the second state. The above-described processing is repeated to acquire image signals of predetermined regions of the sample 90. The predetermined regions of the sample 90 are the entirety of regions of the sample 90 or partial regions which are objects to be observed in the sample 90. As described above, the controller 60 determines regions of the sample 90, which correspond to image signals generated, on the basis of the positional relationship between regions of the samples 90 and regions of the imaging element 50 on which the images are projected.

The controller 60 moves the illuminator 20 or the plurality of microlenses 40 so that respective regions of the sample 90 are included in an image that is formed by at least one of the plurality of microlenses 40. In a case where two images, which are projected on the imaging element 50 by two adjacent microlenses 40, overlap each other, the controller 60 moves the illuminator 20 or the plurality of microlenses 40 so that regions in which two images overlap each other are included in the central portion of the images.

When combining image signals, the controller 60 generates an image signal corresponding to an image formed by each of the plurality of microlenses 40 from an image signal corresponding to the entirety of the imaging plane of the imaging element 50. In a case where there is a gap between two images which are projected on the imaging element 50 by two adjacent microlenses 40, an image signal, which corresponds to an image formed by each of the plurality of microlenses 40, is generated, and thus an influence of the gap is reduced. In a case where two images projected on the imaging element 50 by the two adjacent microlenses 40 overlap each other, the controller 60 generates image signals corresponding to a region other than regions in which two images among images formed by the plurality of microlenses 40 overlap each other. For example, the controller 60 generates an image signal corresponding to the central region of an image formed by each of the plurality of microlenses 40.

Through the above-described processing, the controller 60 generates an image signal which corresponds to an image formed by each of the plurality of microlenses 40, and corresponds to respective regions of the sample 90. The controller 60 combines the image signals corresponding to the respective regions of the sample 90 to acquire image signals of predetermined regions of the sample 90.

At the peripheral portion of an image formed by the microlens 40, quality is poor due to the influence by aberration. At the central portion of an image formed by the microlens 40, a favorable image is obtained. According to this, the controller 60 may generate an image signal, which corresponds to the central region of an image formed by each of the plurality of microlenses 40, from an image signal corresponding to the entirety of the imaging plane of the imaging element 50 regardless of the image overlapping. As the diameter $\phi 2$ of the microlens 40, the controller 60 may apply a diameter, which is smaller than an actual diameter, to Expressions (1) and (4). According to this, the controller 60 can calculate imaging regions of the imaging element 50 in which a favorable image can be acquired, and regions of the sample 90 which correspond to the imaging regions.

Figure 12:
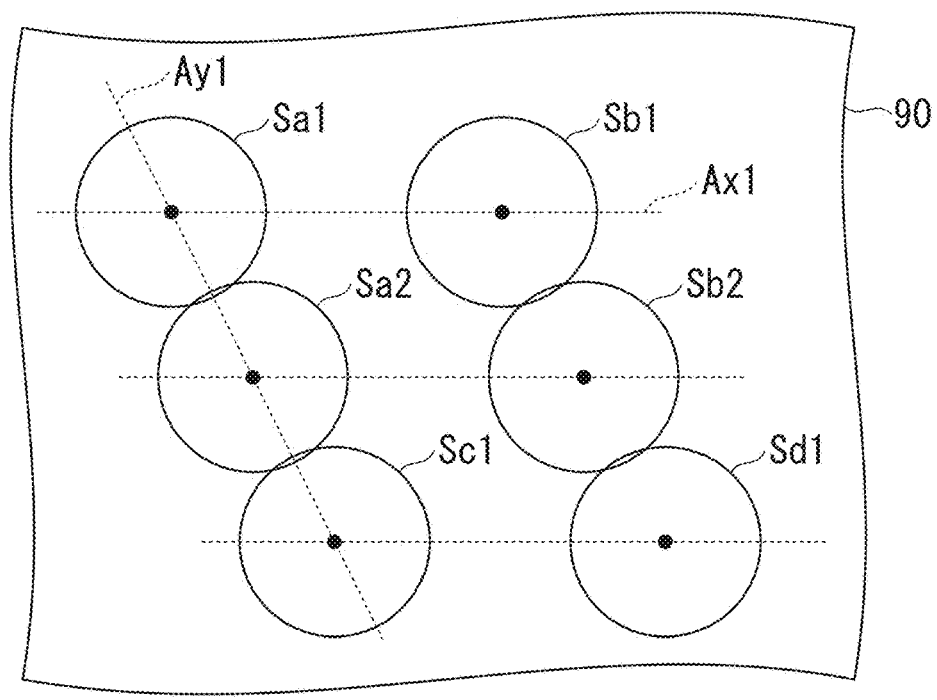
FIG. 12 is a schematic view showing a method of acquiring image signals according to the embodiment of the present invention.

A method of acquiring image signals will be described with reference to FIG. 12. Hereinafter, description will be given of an example in which the plurality of microlenses 40 are moved. FIG. 12 shows regions of the sample 90 which correspond to images projected on the imaging element 50 by the microlens 40. In FIG. 12, only a part of the sample 90 is shown.

An X-axis Ax1 and a Y-axis Ay1 are set in an arrangement direction of the plurality of microlenses 40. The X-axis Ax1 and the Y-axis Ay1 need not be set to be perpendicular to each other. A region Sa1, a region Sb1, a region Sc1 and a region Sd1 are initial regions of the sample 90 when image signals are acquired for the first time. The region Sa1 is a region of the sample 90 which corresponds to an image projected on the imaging element 50 by a microlens A. The microlens A is any one of the plurality of microlenses 40. The region Sb1 is a region of the sample 90 which corresponds to an image projected on the imaging element 50 by a microlens B. The microlens B is a microlens 40, which is adjacent to the microlens A in a direction of the X-axis Ax1, among the microlenses 40. The region Sc1 is a region of the sample 90 which corresponds to an image projected on the imaging element 50 by a microlens C. The microlens C is a microlens 40, which is adjacent to the microlens A in a direction of the Y-axis Ay1, among the microlenses 40. The region Sd1 is a region of the sample 90 which corresponds to an image projected on the imaging element 50 by a microlens D. The microlens D is a microlens 40, which is adjacent to the microlens C in a direction of the X-axis Ax1, among the microlenses 40.

Description will be mainly given of a method of acquiring image signals based on an image projected on the imaging element 50 by the microlens A. The following description is applicable to a method of acquiring image signals based on images projected on the imaging element 50 by other microlenses 40 including the microlens B, the microlens C, and the microlens D. For convenience of explanation, regions of the sample 90 are divided into a plurality of stages.

The plurality of microlenses 40 are disposed at an initial position to acquire image signals of regions of the sample 90 at a first stage. Image signals, which correspond to images of a plurality of regions including the region Sa1, the region Sb1, the region Sc1, and the region Sd1, are acquired. Then, the controller 60 moves the plurality of microlenses 40 in a direction parallel to the X-axis Ax1. During the movement, acquisition of image signals is performed one or more times. When a region of the sample 90, through which light beams condensed by the microlens A are transmitted, overlaps the region Sb1, the acquisition of image signals is stopped. According to this, the acquisition of image signals of regions of the sample 90 at the first stage is terminated.

The plurality of microlenses 40 are disposed at a position different from the initial position to acquire a signals of regions of the sample 90 at a second stage. According to this, light beams, which are transmitted through a region Sa2 of the sample 90, are incident to the microlens A, and light beams, which are transmitted through a region Sb2 of the sample 90, are incident to the microlens B. The region Sa2 is a region that is spaced away from the region Sa1 by an approximately the same distance as a diameter of one region in a direction toward the region Sc1 in parallel to the Y-axis Ay1. The region Sb2 is a region that is spaced away from the region Sb1 by an approximately the same distance as a diameter of one region in a direction toward the region Sd1 in parallel to the Y-axis Ay1.

Image signals, which correspond to images of a plurality of regions including the region Sa1, the region Sb1, the region Sc1, and the region Sd1, are acquired. Then, the controller 60 moves the plurality of microlenses 40 in a direction parallel to the X-axis Ax1. During the movement, acquisition of image signals is performed one or more times. When a region of the sample 90, through which light beams condensed by the microlens A are transmitted, overlaps the region Sb2, the acquisition of image signals is stopped. According to this, the acquisition of image signals of regions of the sample 90 at the second stage is terminated.

Image signals of regions of the sample 90 at a third stage are acquired by the same method as described above. When a region of the sample 90, through which light beams condensed by the microlens A are transmitted, overlaps the region Sc1, acquisition of the entirety of necessary image signals is terminated. In an example shown in FIG. 12, when the acquisition of image signals of regions of the sample 90 at the second stage is terminated, the acquisition of the entirety of necessary image signals is terminated.

For example, image signals are acquired simultaneously with movement of the plurality of microlenses 40. Alternatively, image signals may be acquired in a state in which the plurality of microlenses 40 are stopped after the plurality of microlenses 40 are moved by a predetermined distance.

According to the above-described method, the imaging device 10 can acquire image signals based on the image of the sample 90 with efficiency.

The controller 60 knows the initial position of the plurality of microlenses 40. The controller 60 can determine timing at which acquisition of image signals of regions of the sample 90 at each stage is terminated through determination on whether or not a position of the microlens A is an initial position of the microlens B.

The controller 60 may determine the timing, at which acquisition of image signals of regions of the sample 90 at each stage is terminated, on the basis of image signals corresponding to an image projected on the imaging element 50 by the plurality of microlenses 40. For example, the controller 60 determines whether or not an image projected on the imaging element 50 by the microlens A is the same as an image projected on the imaging element 50 by the microlens B at the initial position on the basis of discontinuity or brightness of images in image signals. In a case where the two images are the same as each other, the acquisition of image signals of regions of the sample 90 at each stage is terminated.

In a case where a magnification of the microlens 40 is one or less, a region of the imaging element 50, on which an image is projected by the microlens 40, is smaller than a region of the sample 90 corresponding to the image. In a case where the magnification of the microlens 40 is one or less, a plurality of images, which are formed by the plurality of microlenses 40, do not overlap each other. Accordingly, in a case where the magnification of the microlens 40 is one less, and image signals based on images projected on the imaging element 50 by the plurality of microlenses 40 are acquired at the entirety of the imaging plane of the imaging element 50, image signals corresponding to the entirety regions of the sample 90 are acquired.

In a case where the magnification of the microlens 40 is one or less, image signals are acquired in a plurality of states including the first state and the second state. In a case where an aggregation of regions of the imaging plane of the imaging element 50, in which image signals are acquired in each of the states, matches the entirety of the imaging plane of the imaging element 50, acquisition of image signals corresponding to the entirety of regions of the sample 90 is terminated. The controller 60 calculates at least one of the irradiation position of light beams from the illuminator 20 and the position of the plurality of microlenses 40 so that images are projected to the entirety of regions of the imaging plane of the imaging element 50 only on the basis of Expression (1) and Expression (2). That is, the controller 60 calculates the diameter 1 of the illuminator 20 and the central position C1 of the illuminator 20 only on the basis of Expression (1) and Expression (2). Alternatively, the controller 60 calculates the diameter $\phi 2$ of the microlens 40 and the central position C2 of the microlens 40 only on the basis of Expression (1) and Expression (2). In a case where the magnification of the microlens 40 is one or less, calculation based on Expression (3) and Expression (4) is not necessary.

The controller 60 may control at least one of the irradiation position of light beams from the illuminator 20 and the position of the plurality of microlenses 40 without using Expressions (1) to (4). That is, the controller 60 may determine an imaging region in the sample 90 on the basis of image signals. The controller 60 may control at least one of the irradiation position of light beams from the illuminator 20 and the position of the plurality of microlenses 40 so that a first imaging region and a second imaging region are different from each other. The first imaging region is the imaging region in the sample 90 through which light beams incident to each of the plurality of microlenses 40 are transmitted in the first state. The second imaging region is the imaging region in the sample 90 through which light beams incident to each of the plurality of microlenses 40 are transmitted in the second state.

For example, the controller 60 determines the same region in a plurality of images on the basis of discontinuity or brightness of images in image signals. In a case where an overlapping region exists in a plurality of images which are simultaneously acquired, the controller 60 generates image signals corresponding to a region other than a region in which two images overlap each other from image signals corresponding to each of the images. The controller 60 moves at least one of the illuminator 20 and the plurality of microlenses 40 so that respective regions of the sample 90 are included in an image formed by at least one of the plurality of microlenses 40.

The imaging device according to each aspect of the present invention need not have a configuration corresponding to at least one of the illuminator drive unit 70 and the lens drive unit 80. The imaging device according to each aspect of the present invention has only to be capable of acquiring image signals corresponding to each of the first state and the second state. An external device of the imaging device may combine first image signals generated in the first state and second image signals generated in the second state. Accordingly, the imaging device according to each aspect of the present invention need not perform combination of the first image signals and the second image signals.

In the embodiment of the present invention, a first angle of light beams incident to each of the plurality of microlenses 40 in the first state and a second angle of beams incident to each of the plurality of microlenses 40 in the second state are different from each other. According to this, the imaging device 10 can set imaging regions of the sample 90 so that arbitrary regions of the sample 90 are included in an image formed by at least one of the plurality of microlenses 40. Accordingly, the imaging device 10 can obtain favorable image signals of the sample 90.

In a case where the illuminator 20 generates parallel light beams, adjustment of a distance between the illuminator 20 and the microlens 40 is simplified.

In a case where the microlens 40 is moved and the illuminator fixed, a failure risk is reduced.

In a case where the controller 60 controls both of the irradiation position of light beams from the illuminator 20 and the position of the plurality of microlenses 40, movement time and a movement distance of the illuminator 20 and the microlenses 40 are reduced.

FIRST MODIFICATION EXAMPLE

Figure 13:
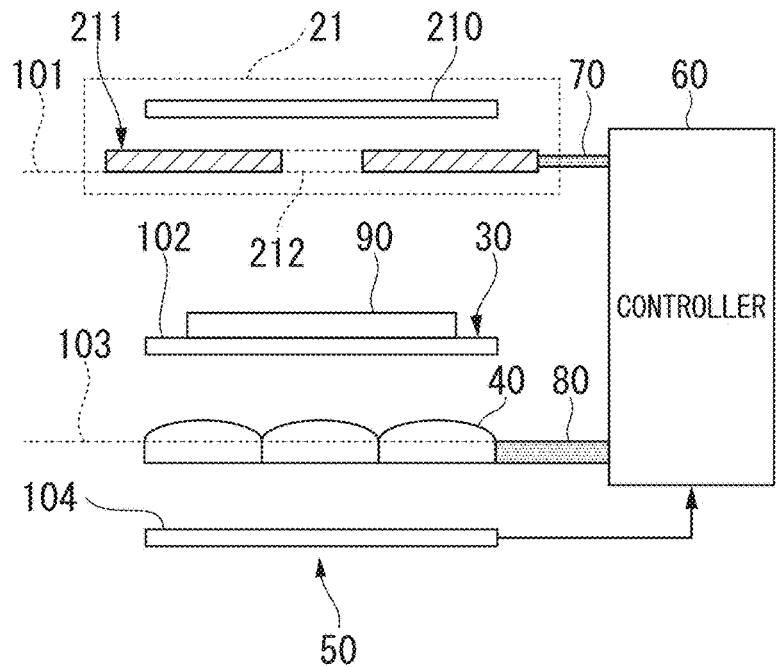
FIG. 13 is a block diagram showing a configuration of an imaging device according to a first modification example of the embodiment of the present invention.

Description will be given of a first modification example of the embodiment of the present invention. FIG. 13 shows a configuration of an imaging device 11 according to the first modification example. As shown in FIG. 13, the imaging device 11 includes an illuminator 21, a stage 30, a plurality of microlenses 40, an imaging element 50, and a controller 60. In addition, the imaging device 11 includes an illuminator drive unit 70 and a lens drive unit 80. In FIG. 13, cross-sections of the illuminator 21, the stage 30, the plurality of microlenses 40, and the imaging element 50 are shown. The cross-sections are perpendicular to the first plane 101 on which the illuminator 21 is disposed.

With regard to the configuration shown in FIG. 13, a difference from the configuration shown in FIG. 1 will be described. In the imaging device 11, the illuminator 20 in the imaging device 10 is changed to the illuminator 21. The illuminator 21 includes a light source 210 and a diaphragm 211.

The light source 210 generates light beams. The light source 210 may be fixed. The diaphragm 211 is disposed between the light source 210 and the sample 90, and includes an opening 212. In addition, the diaphragm 211 is disposed on the first plane 101, and includes the opening 212 in the first plane 101. Light beams from the light source 210 pass through the opening 212. The sample 90 is irradiated with the light beams passing through the opening 212. The controller 60 controls a position of the diaphragm 211 so that a position of the opening 212 in the first state and a position of the opening 212 in the second state are different from each other. The position of the opening 212 in a direction parallel to the first plane 101 in the first state and a position of the opening 212 in a direction parallel to the first plane 101 in the second state are different from each other. The controller 60 controls the position of the diaphragm 211 in a direction parallel to the first plane 101.

The configuration in FIG. 13 is the same as the configuration shown in FIG. 1 except for the difference described above.

Figure 14:
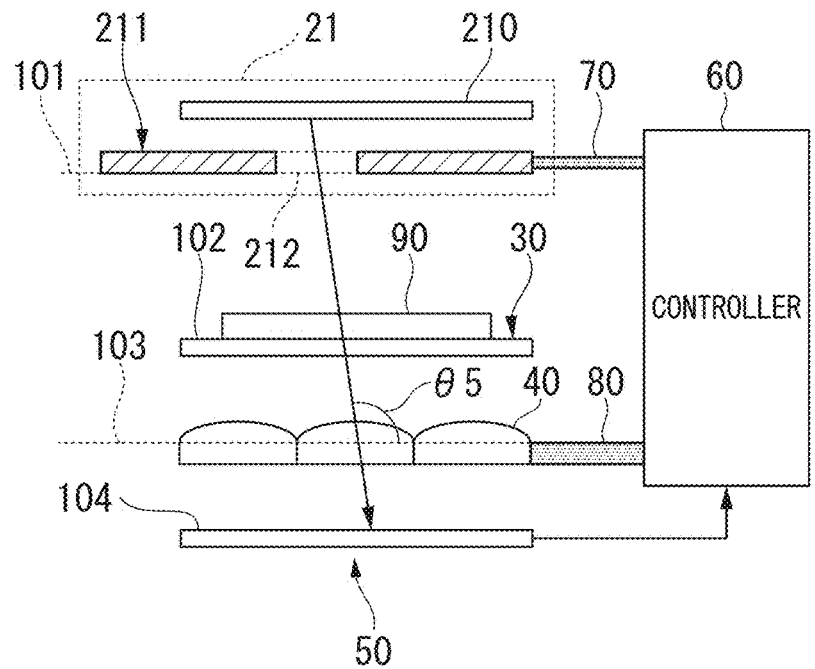
FIG. 14 is a block diagram showing a state of the imaging device in the first state and the second state according to the first modification example of the embodiment of the present invention.
Figure 15:
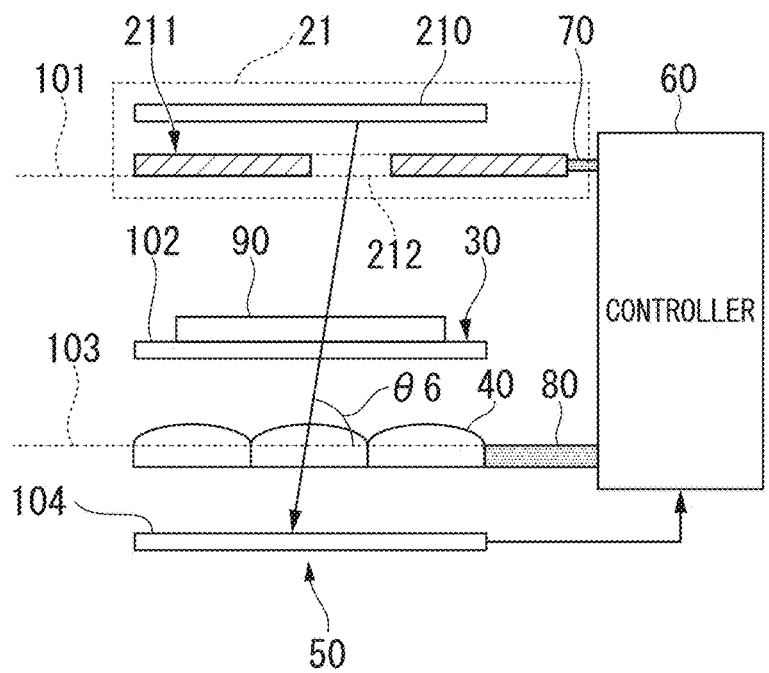
FIG. 15 is a block diagram showing a state of the imaging device in the first state and the second state according to the first modification example of the embodiment of the present invention.

FIG. 14 and FIG. 15 show a state of the imaging device 11 in the first state and the second state. FIG. 14 shows an example of the first state, and FIG. 15 shows an example of the second state. In FIG. 14 and FIG. 15, cross-sections of the illuminator 21, the stage 30, the plurality of microlenses 40, and the imaging element 50 are shown. The cross-sections are perpendicular to the first plane 101 on which the illuminator 21 is disposed. FIG. 14 and FIG. 15 show an example in which the diaphragm 211 is moved in a direction parallel to the first plane 101.

As shown in FIG. 14, in the first state, a first angle of light beams incident to a central microlens 40 among the plurality of microlenses 40 is $\theta 5$. FIG. 15 shows a state after the diaphragm 211 is moved to the right side. When the diaphragm 211 is moved, the opening 212 of the diaphragm 211 is moved. According to this, an angle of light beams incident to the central microlens 40 varies. As shown in FIG. 15, in the second state, a second angle of light beams incident to the central microlens 40 is $\theta 6$. The first angle $\theta 5$ and the second angle $\theta 6$ are different from each other. An angle of light beams incident to the microlens 40 is an angle at which a straight line passing through the center (center of gravity) of the opening 212 in the first plane 101 and the center (principal point) of the microlens 40 intersects the third plane 103.

FIG. 14 and FIG. 15 show a variation of an angle of light beams incident to the central microlens 40. Similarly, an angle of light beams incident to the other microlenses 40 also varies. When the angle of light beams incident to the plurality of microlenses 40 varies, regions of the sample 90 in images that are projected on the imaging element 50 by the plurality of microlenses 40 vary.

In the imaging device 11, the opening 212 is disposed at the central portion of the diaphragm 211. However, the position at which the opening 212 is disposed is not limited to the central portion of the diaphragm 211.

As described above, when the diaphragm 211 is moved, an angle of light beams incident to the plurality of microlenses 40 varies, and regions of the sample 90 in images projected on the imaging element 50 by the plurality of microlenses 40 varies. It is not necessary for the light source 210 to be moved. Since the light source 210 provided with electrical wiring is fixed, a failure risk is reduced.

SECOND MODIFICATION EXAMPLE

Figure 16:
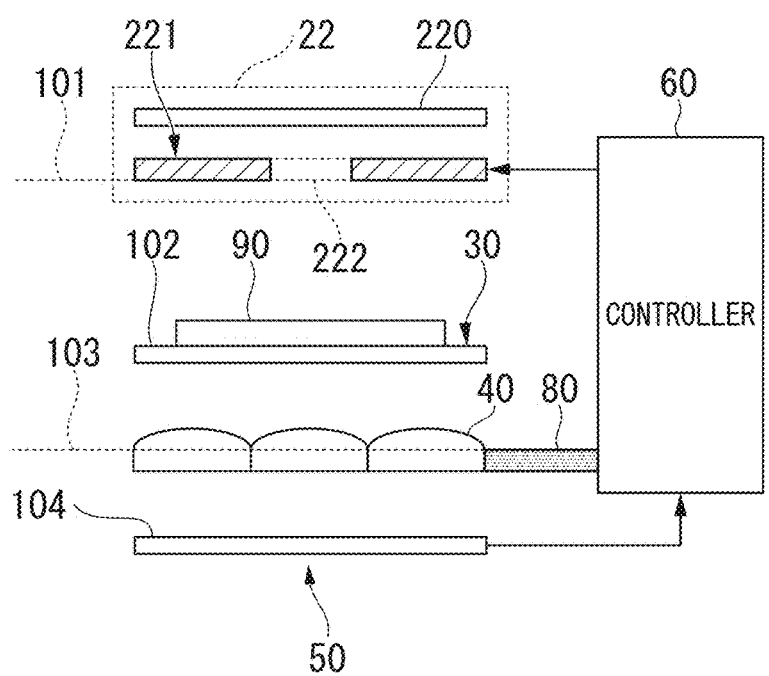
FIG. 16 is a block diagram showing a configuration of an imaging device according to a second modification example of the embodiment of the present invention.

Description will be given of a second modification example of the embodiment of the present invention. FIG. 16 shows a configuration of an imaging device 12 according to the second modification example. As shown in FIG. 16, the imaging device 12 includes an illuminator 22, a stage 30, a plurality of microlenses 40, an imaging element 50, and a controller 60. In addition, the imaging device 12 includes a lens drive unit 80. In FIG. 16, cross-sections of the illuminator 22, the stage 30, the plurality of microlenses 40, and the imaging element 50 are shown. The cross-sections are perpendicular to a first plane 101 on which the illuminator 22 is disposed.

With regard to the configuration shown in FIG. 16, a difference from the configuration shown in FIG. 1 will be described. In the imaging device 12, the illuminator 20 in the imaging device 10 is changed to the illuminator 22. The illuminator 22 includes a light source 220 and a plurality of liquid crystal elements 221. For convenience of illustration, the plurality of liquid crystal elements 221 are shown as an aggregation of a plurality of elements.

The light source 220 generates light beams. The plurality of liquid crystal elements 221 are two-dimensionally arranged between the light source 220 and the sample 90, and enter a transmission state in which light beams are transmitted and a blocking state in which light beams are blocked. The plurality of liquid crystal elements 221 are two-dimensionally arranged on the first plane 101. The light source 220 and the plurality of liquid crystal elements 221 may be fixed. Light beams from the light source 220 are transmitted through one or more liquid crystal elements 221 in a region 222. The liquid crystal element 221 in the region 222 is in the transmission state. In a region in which the plurality of liquid crystal elements 221 are arranged, liquid crystal elements 221 in regions other than the region 222 are in the blocking state. The sample 90 is irradiated with light beams which are transmitted through the liquid crystal element 221 in the transmission state. The controller 60 controls the plurality of liquid crystal elements 221 so that one or more liquid crystal elements 221 disposed in a first region enter the transmission state in the first state and one or more liquid crystal elements 221 disposed in a second region enter the blocking state in the first state. The controller 60 controls the plurality of liquid crystal elements 221 so that one or more liquid crystal elements 221 disposed in a third region different from the first region enter the transmission state in the second state and one or more liquid crystal elements 221 disposed in a fourth region different from the third region enter the blocking state in the second state. The first region and the forth region are not necessarily the same. The second region and the third region are not necessarily the same.

The configuration shown in FIG. 16 is the same as the configuration shown in FIG. 1 except for the difference described above.

Figure 17:
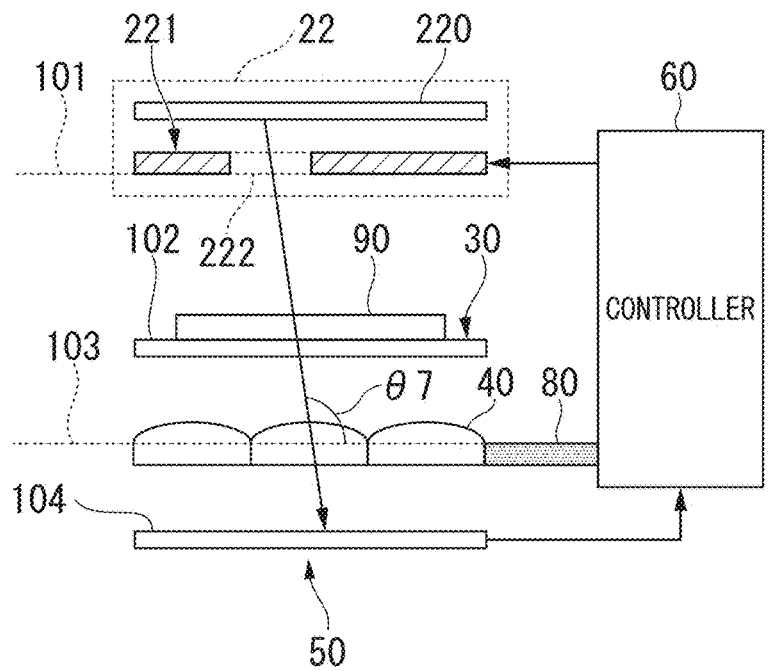
FIG. 17 is a block diagram showing a state: of the imaging device in the first state and the second state according to the second modification example of the embodiment of the present invention.
Figure 18:
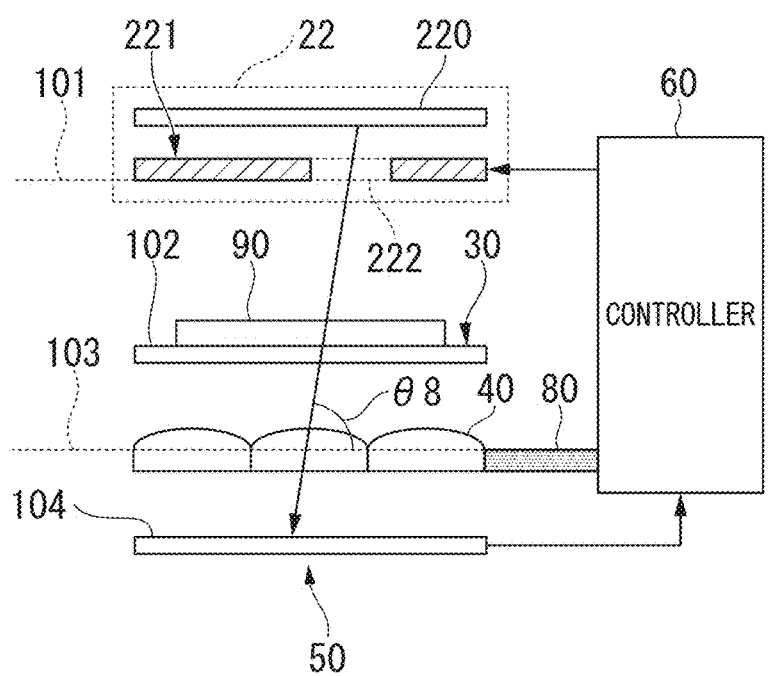
FIG. 18 is a block diagram showing a state of the imaging device in the first state and the second state according to the second modification example of the embodiment of the present invention.
Figure 19:
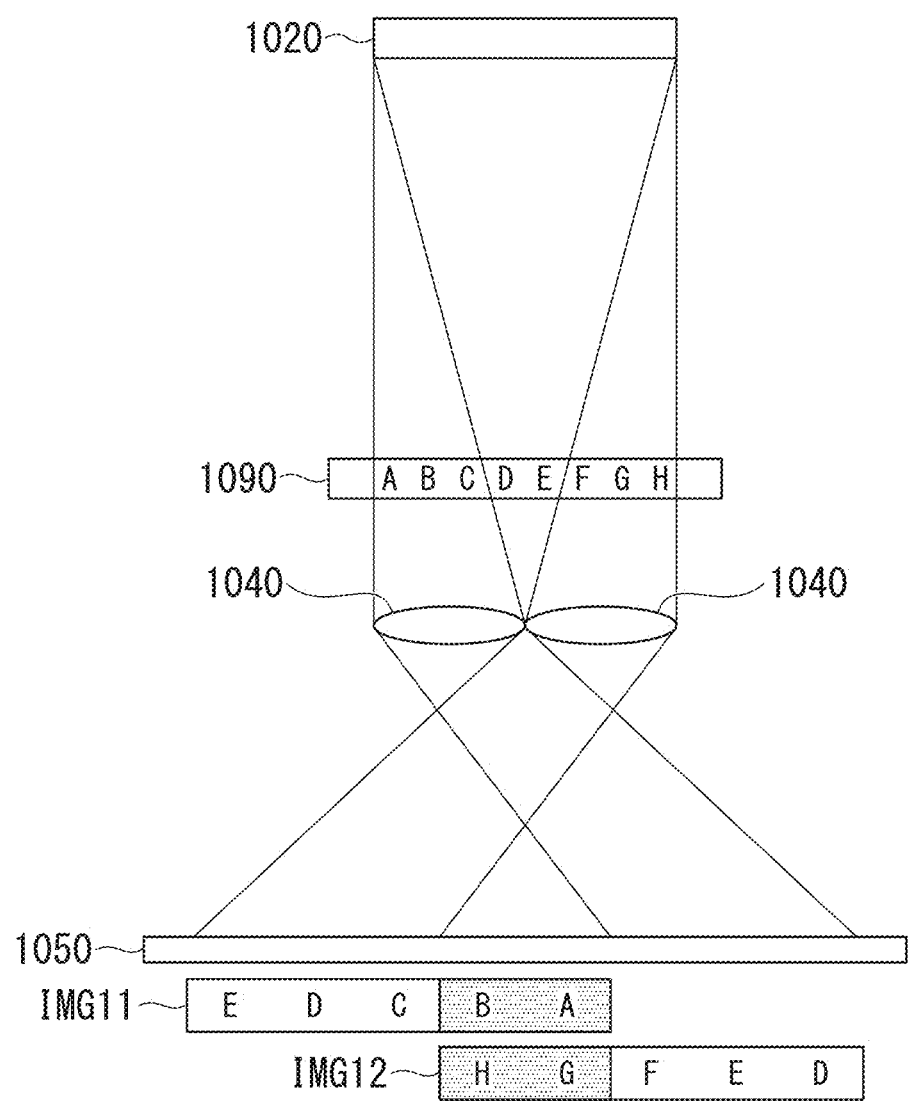
FIG. 19 is a cross-sectional view showing an example in which images formed by two adjacent microlenses overlap each other.

FIG. 17 and FIG. 18 show a state of the imaging device 12 in the first state and the second state, FIG. 17 shows an example of the first state, and FIG. 18 shows an example of the second state. In FIG. 17 and FIG. 18, cross-sections of the illuminator 22, the stage 30, the plurality of microlenses 40, and the imaging element 50 are shown. The cross-sections are perpendicular to a first plane 101 on which the illuminator 22 is disposed. FIG. 17 and FIG. 18 show an example in which the region 222 is moved in a direction parallel to the first plane 101.

As shown in FIG. 17, in the first state, a first angle of light beams incident to the central microlens 40 among the plurality of microlenses 40 is θ7. In FIG. 17, in regions in which the plurality of liquid crystal elements 221 are arranged, a region 222 is a first region, and a region other than the region 222 is a second region. FIG. 18 shows a state after the region 222 is moved to the right side. When the region 222 in which the liquid crystal element 221 in the transmission state is disposed is moved, an angle of light beams incident to the central microlens 40 varies. In FIG. 18, in regions in which the plurality of liquid crystal elements 221 are arranged, the region 222 is a third region, and a region other than the region 222 is a fourth region. As shown in FIG. 18, in the second state, a second angle of light beams incident to the central microlens 40 is θ8. The first angle θ7 and the second angle θ8 are different from each other. The angle of light beams incident to the microlens 40 is an angle at which a straight line passing through the center (center of gravity) of the region in which the liquid crystal element 221 in the transmission state is disposed on the first plane 101 and the center (principal point) of the microlens 40 intersects the third plane 103.

FIG. 17 and FIG. 18 show a variation of an angle of light beams incident to the central microlens 40. Similarly, an angle of light beams incident to the other microlenses 40 also varies. When the angle of light beams incident to the plurality of microlenses 40 varies, regions of the sample 90 in images that are projected on the imaging element 50 by the plurality of microlenses 40 vary.

As described above, when the region 222 in which the plurality of liquid crystal elements 221 in the transmission state is disposed is moved, the angle of light beams incident to the plurality of microlenses 40 varies, and regions of the sample 90 in images that are projected on the imaging element 50 by the plurality of microlenses 40 vary. It is not necessary for the light source 220 to be moved. Since the light source 220 provided with electrical wiring is fixed, a failure risk is reduced. Since the transmission state and the blocking state of the liquid crystal element 221 are switched from each other, it is not necessary for the plurality of liquid crystal elements 221 to be moved. According to this, a failure risk is further reduced.

THIRD MODIFICATION EXAMPLE

Description will be given of a third modification example of the embodiment of the present invention. The third modification example will be described by using the imaging device 10 shown in FIG. 1. The illuminator 20 may include a plurality of LEDs which generate light beams.

The plurality of LEDs are two-dimensionally arranged between the light source and the sample 90, and enters a light-emitting state and a turned-off state. The plurality of LEDs are two-dimensionally arranged on the first plane 101. The sample 90 is irradiated with light beams from one or more LEDs in the light-emitting state among the plurality of LEDs. The controller 60 controls the plurality of LEDs so that one or more LEDs disposed in a fifth region enter the light-emitting state in the first state and one or more LEDs disposed in a sixth region different from the fifth region enter the turned-off state in the first state. The controller 60 controls the plurality of LEDs so that one or more LEDs disposed in a seventh region different from the fifth region enter the light-emitting state in the second state and one or more LEDs disposed in an eighth region different from the seventh region enter the turned-off state n the second state. The fifth region and the eighth region are not necessarily the same. The sixth region and the seventh region are not necessarily the same.

When a region in which the LED in the light-emitting a is disposed is moved, an angle of light beams incident to the plurality of microlenses 40 varies, and regions of the sample 90 in images that are projected on the imaging element 50 by the plurality of microlenses 40 vary. It is not necessary for the plurality of LEDs to be moved. According to this, a failure risk is reduced.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:
1. An imaging device, comprising:
an illuminator configured to generate light beams;
a stage on which a sample is disposed and through which the light beams from the illuminator are transmitted;
a plurality of microlenses which are two-dimensionally arranged, and configured to condense the light beams which are transmitted through the sample and the stage;
an image sensor to which the light beams transmitted through the plurality of microlenses are incident, and which is configured to output image signals based on the light beams; and
a controller configured to control at least one of an irradiation position of the light beams from the illuminator and a position of the plurality of microlenses to realize a first state and a second state, a first angle of the light beams incident to each of the plurality of microlenses in the first state and a second angle of the light beams incident to each of the plurality of microlenses in the second state being different from each other,
wherein the controller is configured to combine a portion of a first image and a portion of a second image, the portion of the first image and the portion of the second image being generated by a same microlens from among the plurality of microlenses, and the controller being configured to combine the portion of the first image and the portion of the second image such that a first region of the sample in the first image overlaps with a second region of the sample in the second image, the first region and the second region being a same region of the sample, and
wherein each of the first image and the second image is an image formed by the plurality of microlenses,
the first image is an image corresponding to the first state, and
the second image is an image corresponding to the second state.
2. The imaging device according to claim 1, wherein the illuminator is configured to generate parallel light beams.
3. The imaging device according to claim 1, wherein the controller is configured to control the position of the plu- rality of microlenses in a direction parallel to a plane that passes through centers of two or more microlenses among the plurality of microlenses.

4. The imaging device according to claim 1, wherein the illuminator includes:
  a light source configured to generate the light beams, and
  a diaphragm that is disposed between the light source and the sample, and includes an opening, and
  wherein the controller is configured to control a position of the diaphragm so that a position of the opening in the first state and a position of the opening in the second state are different from each other.

5. The imaging device according to claim 1, wherein the illuminator includes:
  a light source configured to generate the light beams, and
  a plurality of liquid crystal elements which are two-dimensionally arranged between the light source and the sample, and configured to enter a transmission state in which the light beams are transmitted and a blocking state in which the light beams are blocked,
  wherein the controller is configured to control the plurality of liquid crystal elements so that the liquid crystal element among the plurality of liquid crystal elements disposed in a first region enters the transmission state in the first state and the liquid crystal element among the plurality of liquid crystal elements disposed in a second region different from the first region enters the blocking state in the first state, and
  wherein the controller is configured to control the plurality of liquid crystal elements so that the liquid crystal element disposed in a third region different from the first region enters the transmission state in the second state and the liquid crystal element disposed in a fourth region different from the third region enters the blocking state in the second state.

6. The imaging device according to claim 1, wherein the controller is configured to control both of the irradiation position of the light beams from the illuminator and the position of the plurality of microlenses.

7. The imaging device according to claim 1, wherein:
  the controller is configured to calculate at least one of the irradiation position of the light beams from the illuminator and the position of the plurality of the microlenses in the first state,
  the controller is configured to calculate at least one of the irradiation position of the light beams from the illuminator and the position of the plurality of microlenses in the second state, and
  the controller is configured to control at least one of the irradiation position of the light beams from the illuminator and the position of the plurality of microlenses on the basis of the calculated positions.

8. The imaging device according to claim 1, wherein:
  the controller is configured to determine an imaging region in the sample on the basis of the image signals,
  the controller is configured to control at least one of the irradiation position of the light beams from the illuminator and the position of the plurality of microlenses so that a first imaging region and a second imaging region are different from each other,
  the first imaging region is the imaging region in the sample through which the light beams incident to each of the plurality of microlenses are transmitted in the first state, and
  the second imaging region is the imaging region in the sample through which the light beams incident to each of the plurality of microlenses are transmitted in the second state.

9. The imaging device according to claim 1, each of the portion of the first image and the portion of the second image has a first end and a second end opposite the first end along a direction of relative movement between the illuminator and the microlenses, and
  wherein the controller is configured to combine the portion of the first image and the portion of the second image so that the first region, which is a region included at the first end of the first image, and the second region, which is a region included at the second end of the second image, overlap each other.

10. An imaging device, comprising:
  an illuminator configured to generate light beams;
  a stage on which a sample is disposed and through which the light beams from the illuminator are transmitted;
  a plurality of microlenses which are two-dimensionally arranged, and configured to condense the light beams which are transmitted through the sample and the stage;
  an image sensor to which the light beams transmitted through the plurality of microlenses are incident, and which is configured to output image signals based on the light beams; and
  a controller configured to control at least one of an irradiation position of the light beams from the illuminator and a position of the plurality of microlenses to realize a first state and a second state, a first angle of the light beams incident to each of the plurality of microlenses in the first state and a second angle of the light beams incident to each of the plurality of microlenses in the second state being different from each other,
  wherein the controller is configured to combine a portion of a first image and a portion of a second image, the portion of the first image and the portion of the second image being generated by a same microlens from among the plurality of microlenses,
  wherein the controller is configured to cut out a region from an image formed by each of the plurality of microlenses that does not overlap with images formed by the other microlenses, and to generate the first image and the second image,
  each of the first image and the second image is an image formed by the plurality of microlenses,
  the first image is an image corresponding to the first state, and
  the second image is an image corresponding to the second state.

11. The imaging device according to claim 10, wherein the controller is configured to cut out a central region as the region from the image formed by each of the plurality of microlenses, and to generate the first image and the second image.

* * * * *